United States Patent [19]
Briggs et al.

[11] Patent Number: 5,773,288
[45] Date of Patent: *Jun. 30, 1998

[54] PLANT GENES AFFECTING GIBBERELLIC ACID BIOSYNTHESIS

[75] Inventors: Steven P. Briggs, Des Moines; Robert J. Bensen, Grimes, both of Iowa

[73] Assignee: Pioneer Hi-Bred International, Inc., Des Moines, Iowa

[ * ] Notice: The term of this patent shall not extend beyond the expiration date of Pat. No. 5,612,191.

[21] Appl. No.: 405,254

[22] Filed: Mar. 16, 1995

Related U.S. Application Data

[63] Continuation-in-part of Ser. No. 261,465, Jun. 17, 1994, Pat. No. 5,612,191.
[51] Int. Cl.$^6$ .......................... C12N 15/82; C12N 15/29; C07K 14/415
[52] U.S. Cl. .................. 435/320.1; 435/69.1; 530/376; 536/23.2
[58] Field of Search .............................. 435/172.3, 69.1, 435/320.1; 536/23.2; 530/376

[56] References Cited

FOREIGN PATENT DOCUMENTS

WO/9316096   8/1993   WIPO .

OTHER PUBLICATIONS

Bensen et al., "Cloning Gibberellin Biosynthetic Genes from Maize", Joint Annual Meeting of the American Soc. of Plant Physiologists and the Canadian Soc. of Plant Physiologists, Abstract, Jul. 31, Aug. 4, 1993, p. 8.
Bensen et al., "Cloning Gibberellin Acid Biosynthetic Genes from Maize", Annual Meeting of the American Soc. of Plant Physiologists, Abstract, Aug. 1–5, 1992, p. 19.
Altschul et al., Basic Local Alignment Search Tool, *J. Mol. Biol.*, 215:403–410, (1990).
Barendse et al., The biosynthesis of gibberellin precursor ent–kaurene in cell–free extracts . . . *J. Plant Growth Regul.*, 2:165–175, (1983).
Barkan, et al., Inactivation of Maize Transposon Mu Suppress . . . , *Proc. Natl. Acad. Sci. USA*, 88:3502–06, (1991).
Beavis, W.D. et al., Quantitative Trait Loci for Plant Height in Four Poppulations, *Theor. Appl. Genet.*, 83:141–145, (1991).
Buckner et al., Cloning of the y1 Locus of Maize, a Gene Involved . . . , *The Plant Cell* 2:867–876, (1990).
Chandler et al., DNA Modification of a Maize Transposeable Element Correlates with a Loss of Activity, *Proc. Natl. Acad. Sci. USA*, 83:1767–1771, (1986).
Cheng et al., Organ Initiation and the Development of Unisexual Flowers in Then Tassel and Ear of *Zea Mays*, *Amer. J. Bot.*, 70:450–462, (1983).
Chomczynski, P. and Sacchi, N., *Anal. Biochem.*, 162, 156, (1987).
Coolbaugh, Sites of Gibberellin Biosynthesis in Pea Seedlings, *Plant Physiol.*, 78:655–657, (1985).

Dellaporta et al., A Plant DNA Minipreparation: Version II, *Plant Mol. Biol. Rep.*, 1:4;19–21, (1983).
Duncan et al., Properties of Kaurene Synthetase from Marah Macrocarpus Endosperm: Evidence for the Participation of Separate but Interacting Enzymes, *Plant Physiol.*, 68:1128–1134, (1981).
Emerson et al., Genetic Interrelations of Two Andromonecious Types of Maize, *Genetics*, 7:203–227, (1982).
Facchini et al., Gene Family for an Elicitor–Induced Sesquiterpene Cyclase in Tobacco, *Proc. Natl. Acad. Sci. USA*, 89:11088–11092, (1992).
Fujioka et al., Qualitative and Quantitative Analysis of Gibberellins in Vegetative Shoots of Normal, dwarf–1, dwarf–2 . . . , *L. Plant Physiol.*, 88:1367–1372, (1988).
Han et al., Molecular Cloning and Characterization of lojap (ij) . . . , *The EMBO Jrnl.*, 11:4037–4046, (1992).
Hedden et al., Hormones of Young Tassels of *Zea Mays*, *Phytochemistry*, 21:391–393, (1982).
Johal et al., Reductase Activity Encoded By the HM1 Disease Resistance Gene in Maize, *Science*, 258:985–987, (1992).
McCarty et al., Molecular Analysis of Viviparous–1: An Abscicis Acid–. . . , *The Plant Cell*, 1:523–532, (1989).
McLaughlin et al., Cloning of a Mutable bz2 Allele of Maize by Transposon . . . , *Genetics*, 117:771–776, (1987).
Martienssen et al., Molecular Cloning of Maize Gene Involved . . . , *The EMBOJ Jrnl.*, 8:6;1633–1639, (1989).
Metzger et al., Effect of Photoperiod on the Levels of Endogenous Gibberellins In Spinach as Measured by . . . , *Plant Physiol.*, 66:844–846, (1980).
Metzger et al., Photoperiodic Control of Gibberellin Metabolism in Spinach, *Plant Physiol.*, 69:287–291, (1982).
O'Reilly et al., Molecular Cloning of the a1 Locus of *Zea Mays* . . . , *The EMBOJ Jrnl.*, 4:4;877–882, (1985).
Pasternak et al., Sequence Similarity Searches, Multiple Sequence Alignments, and Molecular Tree Building, *Methods in Plant Molecular Biology and Biotechnology*, CRC Press, Inc., 251–267, (1993).
Rood et al., Gibberellins: A Phytohormonal Basis for Heterois in Maize, *Science*, 241:1216–1218, (1988).

(List continued on next page.)

*Primary Examiner*—Che S. Chereskin
*Attorney, Agent, or Firm*—Foley & Lardner

[57] ABSTRACT

Genes controlling gibberellic biosynthesis are used in genetic engineering to alter plant development. Alterations in the nature or quantity of products of the genes affects plant development. A family of An genes in monocots encodes a cyclase involved in the early steps of gibberellic acid (GA) biosynthesis. Members of the family are identified in wheat, barley, sorghum and maize. Two members of the family, the genes An1 and An2, are identified in maize. The An1 gene is cloned and the function of the gene is characterized. An2 is isolated and identified by homology to An1. Using recombinant genetic technology, GA levels are manipulated. Changes in GA levels alter monocot plant phenotypes, for example, increasing or decreasing height and fertility.

7 Claims, 14 Drawing Sheets

OTHER PUBLICATIONS

Simcox et al., Kaurene Synthetase from Plastids of Developing Plant Tissues, *Biochem. & Biophys. Res. Comm.*, 66:1;166–172, (1975).

Sun et al., Cloning the Arabidopsis GA1 Locus by Genomic Subtraction, *The Plant Cell*, 4:119–128, (1992).

Suzuki et al., Metabolism of Ent–kaurene to Gibberellin $A_{12}$–aldehyde in Young Shoots of Normal Maize, *Plant Physiol.*, 98:602–610, (1992).

Walbot et al., Regulation on Mu Element Copy Number in Maize Lines with an Active or Inactive Transposable Element System, *Mol. Gen. Genet.*, 211:27–34, (1988).

Walbot, Strategies for Mutagenesis and Gene Cloning Using Transposon Tagging and T–DNA Insertional Mutagenesis, *Ann. Rev. Plant Physiol.*, 43:49–82, (1992).

Bensen, *Maize Genetics Cooperation Newsletter*, 66:51, (1992).

Bensen, *Maize Genetics Cooperation Newsletter*, 67:53, (1993).

Maniates, *Molecular Cloning*, a Laboratory Manual, Cold Spring Harbor Laboratory, 388–89 (1982).

Bensen, et al., Cloning and Characterization of the Maize An1 Gene, *The Plant Cell*, 7:75–84, (1995).

FIG. 2A

```
  1   ........MPYPHPYPWQSSPRRRRRG..RDGAPRQPQARRVVERAAAGP   41
           : ::        ::          :::    :  :
  1   MSLQYHVLNSIPSTTFLSSTKTTISSFLTISGSPLNVAR...DKSRSGS   47

42   GHATTQQPDNVSSAKVFQTSRVETESKLRNGRKPQDLEDEHQAEEAELQ   91
        :  :  : : :      :      :   :    : ::  :::
 48   IHCSKLRTQEYINSQEVQHDLPLIHEWQQLQGEDAPQISVG..SNSNAFK   95

92   PLIDQVRAMLRSMNDGDTSASAYDTAWVAMVPKVGGDGAQPQFPATVRW   141
       :   : :::  :  ::: ::|||:|||:||              :::
 96   EAVKSVKTILRNLTDGEITISAYDTAWVALI.....DAGDKTPAFPSAVKW   141

142   IVDHQLPDGSWGDSALFSAYDRMINTLACVVALTKWSLEPARCEAGLSFL   191
       :|:::||||||||| ||:||||:||||||||||||:|: :: ::  ::
142   IAENQLSDGSWGDAYLFSYHDRLINTLACVVALRSWNLFPHQCNKGITFF   191

192   HENMWRLAEEEAESMPIGFEIAFPSLIQTARDLGVVDFPYGHPALQSIYA   241
       ::| |::: :|:: ||||| |:||||: |:| : ::|| || :||:|||
192   RENIGKLEDENDEHMPIGFEVAFPSLLEIARGIN.IDVPYDSPVLKDIYA   240

242   NREVKLKRIPRDMMHRVPTSILHSLEGMPDLDWPRLLNLQSCDGSFLFSP   291
       ::||||| ||||:|:|:|| ||||||||: |||| :|:||||:|||||
241   KKELKLTRIPKEIMHKIPTTLLHSLEGMRDLDWEKLIKLQSQDGSFLFSP   290
```

FIG. 2B

```
292 SATAYALMQTGDKKCFEYIDRIVKKFNGGVPNVYPVDLFEHIWVDRLER 341
    :||::|:|:||  :||  :|:::|||||||||:|:|||||:||||||
291 SSTAFAFMQTRDSNCLEYLRNAVKRFNGGVPNVFPVDLFEHIWIVDRLQR 340

342 LGISRYFQREIEQCMDYVNRHWTEDGICWARKSNVKDVDDTAMAFRLLRL 391
    ||||||| ::|: ||||:||:||:|||||| ::|:|:|||||||||||
341 LGISRYFEEIKECLDYVHRYWTDNGICWARCSHVQDIDDTAMAFRLLRQ 390

392 HGYNVSPSVFKNFEKDGEFFCFVGQSTQAVTGMYNLNRASQISFQGEDVL 441
    |||:||| ||||||:||||||||||:|||||| ||:||||| :  |::|
391 HGYQVSADVFKNFEKEGEFFCFVGQSNQAVTGMFNLYRASQLAFPREEIL 440

442 HRARVFSYEFLRQREEQGMIRDKWIVAKDLPGEVQYTLDFPWYASLPRVE 491
    :: |:||| ||:|||| :|:|||||:|||||| |  :| :||||||||
441 KNAKEFSYNYLLEKREEELIDKWIIMKDLPGEIGFALEIPWYASLPRVE 490

492 ARTYLDQYGGKDDVWIGKTLYRMPLVNNDTYLELAIRDFNHCQALHQLEC 541
    :|:|:||||| :|||||||||||| ||: ||||||:| ::||| ||||||
491 TRFYIDQYGGENDVWIGKTLYRMPYVNNNGYLELAKQDYNNCQAQHQLEW 540
```

FIG. 2C

```
542 NGLQTWYKDNCLDAFGVEPQDVLRSYFLAAACIFEPSRAAERLAWARTSM 591
    ::.:||.||:||    ||.:  ::||:|||:.:||:||.||:.
541 DIFQKWYEENRLSENGVRRSELLECYYLAAATIFESERSHERMVWAKSSV 590

592 IANAISTHLRDISEDKKRL......ECFVHCLYEENDVS....WLKRNPND 632
    :..:::|| ||:|: :  .      :|:|.|  .:::      |||:
591 LVKAISSSFGESSDSRRSFSDQFHEYIANARRSDHHFNDRNMRLDR.PGS 639

633 VILERALRRLINLIAQEALPIHEGQ.RFIHSLLSLAWTEWMLQKANKEEN 681
    |:  : ||  :|:::   :|:.    |||.|:  . :|| 
640 VQASRLAGVLIGTLNQMSFDLFMSHGRDVNNLLYLSWGDWM........E 681

682 KYHKCSGIEPQYMVHDRQTYLLLVQVIEICAGRIGEAVSMINNKDNDWFI 731
    |:  :        :|:|          ELMVKMI......     :|:.
682 KWKLYGDEGEG...............ELMVKMI.........ILMKNNDLTNFFT 712

732 QLTCATCDSLNHRMLLSQDTMK......NEARINWIEKEIELNMQELAQS 775
    :  :    : .|| :| :|         .:|:||  ||:|::: .|:
713 HTHFVRLAEIINRICLPRQYLKARRNDEKEKTIKSMEKEMG.KMVELALS 761

776 LLLRCDEKTSNKKTIKKTLWDVLRSLYYATHSPQHMIDRHVSRVIFEPV 823
    :|:|:|: .|.: :||:|||||:||.|.|:|| . |:||||:|||||
762 .....ESDTFRDVSITFLDVAKAFYYFALCGDHL.QTHISKVLFQKV 802
```

FIG. 3A

```
GAATTCCGCT AGCTCTTGCT TTGTTGTGTG TCCTGATGGT CGAGTTCCTC ACCGTGCTTT    60
TGCTTTTCTG CTTTCACTTG CCTGCAGCTG CAGCTCGTCA ATCAGGTCCA TGCCGTATCC   120
GCATCCGTAT CCGTGGCAAA GCAGCAGGAG GAGGAGGAGG AGGCGCGGGC GCGACGGGGC   180
CCCGGCGGCA CCTCAGGCTC GCCGGGTGGT GGAGCGCGCA GCAGCAGGCC CCGGCCACGC   240
GACGACAACG CAGCAGCCCG ACAACGTCTC CAGTGCTAAA GTGTTCCAGA CCAGCCGTGT   300
GGAAACCGAG TCGAAATTGC GAAATGGCAG GAAACCACAA GACCTTGAGG ATGAGCACCA   360
GGCTGAGGAG GCAGAGCTGC AGCCACTTAT CGACCAGGTG AGGGCGATGC TACGGTCGAT   420
GAACGACGGG GATACCAGCG CCTCGGCGTA CGACACGGCG TGGGTGGCGA TGGTGCCGAA   480
GGTGGGCGGC GACGGGCGGC CCCAGCCCCA GTTCCCGGCC ACCGTGCGCT GGATCGTGGA   540
CCACCAGCTG CCCGACGGCT CCTGGGGCGA CTCGGCCCTG TTCTCCGCCT ACGACCGCAT   600
GATCAACACC CTCGCCTGCG TCGTCGCGCT GACCAAGTGG TCGCTGGAGC CCGGCGAGGTG   660
CGAGGCGGGG CTCTCGTTCC TGCACGAGAA CATGTGGAGG CTAGCGGAGG AGGAGGCGGA   720
GTCGATGCCC ATCGGCTTCG AGATCGCCCT CCCTTCTCTC ATCCAGACGG CTAGGGACCT   780
GGGCGTCGTC GACTTCCCGT ACGGACACCC GGCGCTGCAG AGCATATACG CCAACAGGGA   840
AGTCAAGCTG AAGCGGATCC CAAGGGACAT GATGCACAGG GTCCCGACGT CCATCCTGCA   900
CAGCCTTGAA GGGATGCCTG ACCTGGACTG GCCGAGGCTT CTGAACCTCC AGTCCTGCGA   960
```

FIG. 3B

```
CGGCTCCTTC TTGTTCTCTC CTTCGGCTAC CGCTTACGCG CTGATGCAAA CCGGTGACAA    1020
GAAGTGCTTC GAATACATCG ACAGGATTGT CAAAAAATTC AACGGGGGAG TCCCCAATGT    1080
TTATCCGGTC GATCTTTTCG AGCACATCTG GGTTGTGGAT CGGTTGGAGC GACTCGGGAT    1140
CTCCCGCTAC TTCCAACGAG AGATTGAGCA GTGCATGGAC TATGTGAACA GGCACTGGAC    1200
TGAAGATGGG ATTTGCTGGG CTAGGAAATC CAATGTGAAG GATGTGGATG ACACAGCTAT    1260
GGCTTTCCGA CTACTAAGGC TACATGGATA CAATGTCTCT CCAAGTGTGT TTAAGAACTT    1320
TGAGAAAGAT GGAGAGTTCT TTTGTTTTGT GGGCCAATCG ACTCAAGCCG TCACTGGGAT    1380
GTATAACCTC AACAGAGCCT CTCAGATAAG TTTTCAAGGA GAGGATGTAT TGCATCGTGC    1440
TAGGGTTTTC TCGTATGAGT TTCTGAGACA GAGAGAAGAA CAAGGCATGA TCCGTGATAA    1500
ATGGATCGTT GCCAAGGATC TACCTGGCGA GGTGCAATAT ACACTAGACT TCCCTTGGTA    1560
TGCAAGCTTG CCTCGTGTAG AGGCAAGAAC CTATCTAGAT CAATATGGTG GTAAAGATGA    1620
CGTTTGGATT GGAAAGACAC TCTACAGGAT GCCTCTTGTG AATAACGACA CATATCTAGA    1680
GTTGGCAATA AGGGATTTCA ACCATTGCCA AGCTCTGCAT CAGCTTGAGT GTAATGGGCT    1740
GCAAACGTGG TACAAGGATA ATTGCCTTGA CGCTTTTTGA GTAGAACCAC AAGATGTTTT    1800
AAGATCTTAC TTTTTAGCTG CTGCTTGCAT TTTTGAACCT AGCCGTGCTG CTGAGCGGCT    1860
TGCATGGGCT AGAACGTCAA TGATTGCCAA TGCCATTTCT ACACATCTTC GTGACATTTC    1920
GGAAGACAAG AAGAGATTGG AATGTTTCGT GCACTGTCTC TATGAAGAAA ACGATGTATC    1980
```

FIG. 3C

```
ATGGCTTAAA CGAAATCCTA ATGATGTTAT TCTTGAGAGG GCACTTCGAA GATTAATTAA   2040
CTTATTAGCA CAAGAAGCAT TGCCAATTCA TGAAGGACAA AGATTCATAC ACAGTCTATT   2100
GAGTCTTGCA TGGACCGAAT GGATGTTGCA AAAGGCAAAT AAAGAAGAAA ACAAATATCA   2160
CAAATGCAGT GGTATAGAAC CACAATACAT GGTTCATGAT AGGCAAACAT ACTTACTTTT   2220
AGTTCAGGTT ATTGAGATTT GTGCTGGACG AATTGGTGAG GCTGTGTCAA TGATAAACAA   2280
CAAGGATAAT GATTGGTTTA TTCAACTCAC ATGTGCTACT TGTGACAGTC TTAACCATAG   2340
GATGTTACTG TCCCAGGATA CTATGAAGAA TGAAGCAAGA ATAAATTGGA TTGAGAAGGA   2400
AATCGAGTTG AATATGCAAG AGCTTGCTCA ATCTCTCCTT TTGAGATGTG ATGAGAAAAC   2460
TAGCAATAAG AAGACCAAGA AAACCTTATG GGATGTCCTA AGAAGTTTAT ACTATGCTAC   2520
TCATTCCCCA CAACATATGA TCGATAGACA TGTTTCCAGA GTTATCTTTG AGCCTGTTTA   2580
AAAATGTTTA AGTGGTAGAC CATTATGTTA GGTGTAAATG TGTACATAAA AGTTATCATA   2640
AGGAGTAATG GTAGCAGAAG CATGCAGTTG TAAGTTTATT TGTTGCTTAG AATAGAAATT   2700
AGTGTAGCTA TAATATCAAG AATGTTCCTA TATAAGTAAT CATATTATGG ATAGAGGTGT   2760
TCATATGAAT AATAAAAAGG AATC                                         2784
```

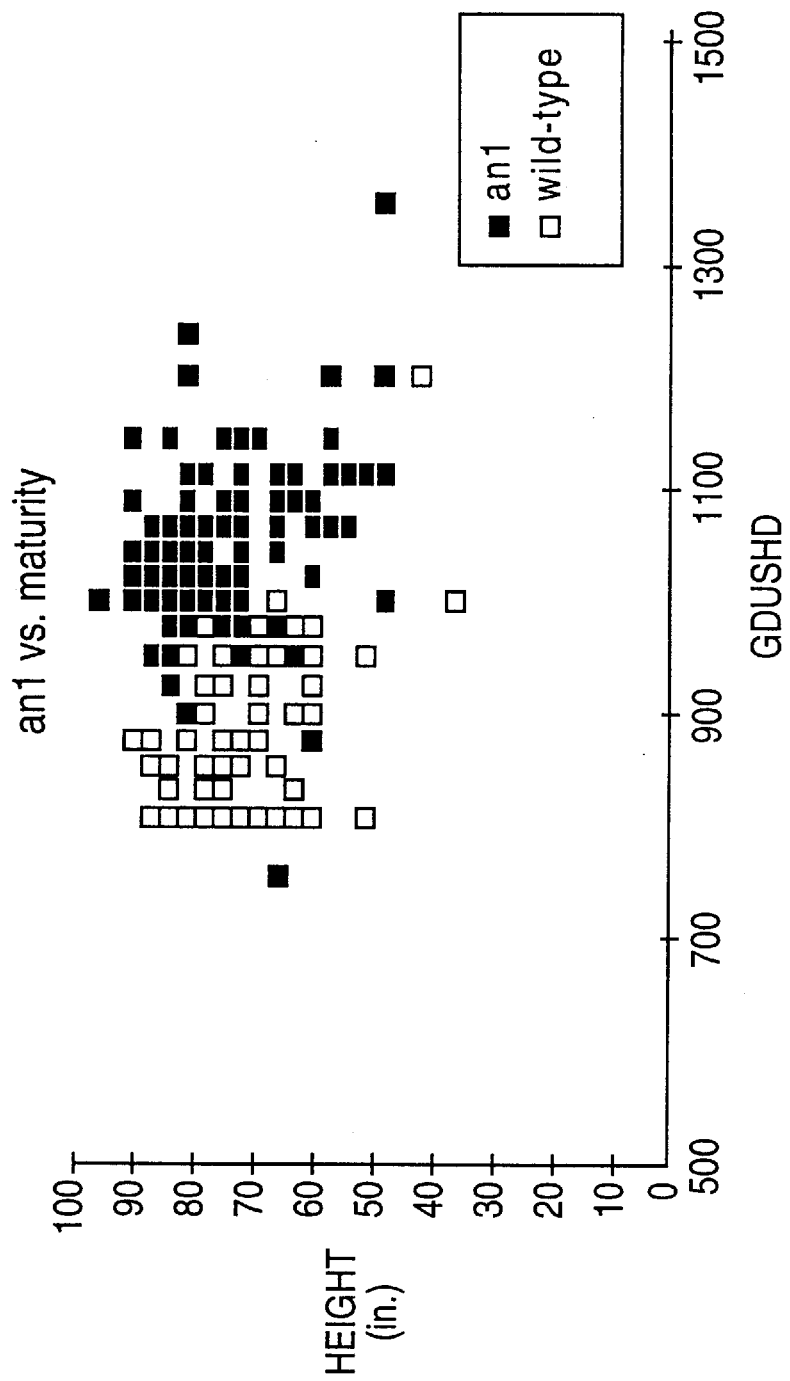

FIG. 6

```
1410 GAGGAGGCGGAGTCGATGCCCATCGGCTTCGAGATCCCCTTCCCTTCTCT 1459
                              ||||||||||||||||||||||||
   1 ........................CTTCGAGATCGCCTTCCCTTCTCT 24
1460 CATCCAGACGGCTAGGGACCTGGGCGTCGTCGACTTCCCGTACGGACACC 1509
     ||||   ||   |   ||||||||| | |||||||||||||||    ||||
  25 CATCGAACTAGCCAAGAGTCTGGGCGTGGACGACTTCCCGTACGACCACC 74
1510 CGGCGCTGCAGAGCATATACGCCAACAGGGAAGTCAAGCTGAAGCGGATC 1559
     |||  |||||  | ||||||  | | |||| |||| ||||| ||||
  75 AGGCTTTGCAGGGAATATACTCGAGCAGGGAGATCAAGATGAAGAGGATT 124
1560 CCAAGGGACATGATGCACAGGGTCCCGACGTCCATCCTGCACAGCCTTGA 1609
     ||  |||  ||||||||| ||| ||  || |||| ||||||||  ||
 125 CCTAAGGAAGTGATGCACACGGTTCCCACATCCATTCTCCACAGCCTGGA 174
1610 AGGGATGCCTGACCTGGACTGGCCGAGGCTTCTGAACCTCCAGTCCTGCG 1659
     ||||||||| |   || ||||||  |||  ||| ||| || |||||  |||
 175 AGGGATGCCCGGGCTAGACTGGGCGAAGCTGCTGAAACTGCAGTCGAGCG 224
1660 ACGGCTCCTTCTTGTTCTCTCCTTCGGCTACCGCTTACGCGCTGATGCAA 1709
     ||||  |||||| | ||||| ||  ||||| |||||| || || ||||
 225 ACGGGTCCTTCCTCTTCTCACCCGCGGCCACCGCGTACGCTCTCATGAAC 274
1710 ACCGGTGACAAGAAGTGCTTCGAATACATCGACAGGATTGTCAAAAAATT 1759
     ||||| ||| | | |||||||| ||||||||||||| | ||||  ||||
 275 ACCGGCGACGACAGGTGCTTCAGCTACATCGACAGGACAGTCAAGAAATT 324
1760 CAACGGGGGAGTCCCCAATGTTTATCCGGTCGATCTTTTCGAGCACATCT 1809
     |||||| ||||| ||| |||| ||  ||  || ||||||||||||||| |
 325 CAACGGAGGAGTGCCCAACGTCTACCCCGTGGACCTTTTCGAGCACATAT 374
1810 GGGTTGTGGATCGGTTGGAGCGACTCGGGATCTCCCGCTACTTCCAACGA 1859
     ||| || ||||| ||||||||||| ||||||||||||||||||||| ||
 375 GGGCTGTCGATCGCCTGGAGCGTCTCGGGATCTCCCGCTACTTCCAGAAA 424
1860 GAGATTGAGCAGTGCATGGACTATGTAACAGGCACTGGACTGAAGATGG 1909
     |||||||||||||||||||||| |||||||||||||||||||||||||||
 425 GAGATTGAGCAGTGCATGGACTACGTAACAGGCACTGGACTGAAGATGG 474
1910 GATTTGCTGGGCTAGGAAATCCAATGTGAAGGATGTGGATGACACAGCTA 1959
     ||||||||||||||
 475 GATTTGCTGGGCTA............................... 488
```

FIG. 7
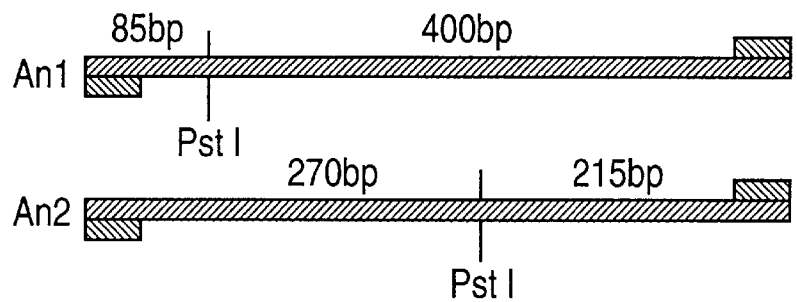
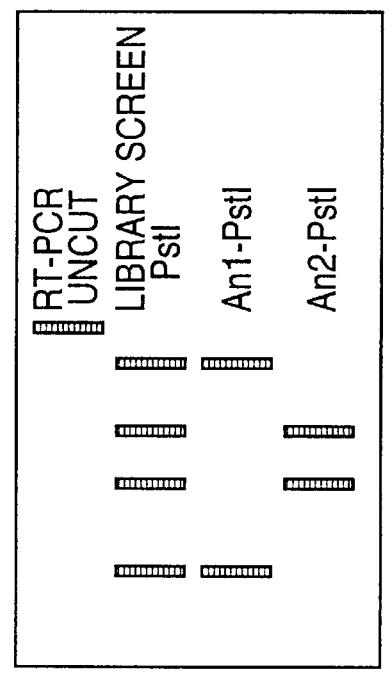
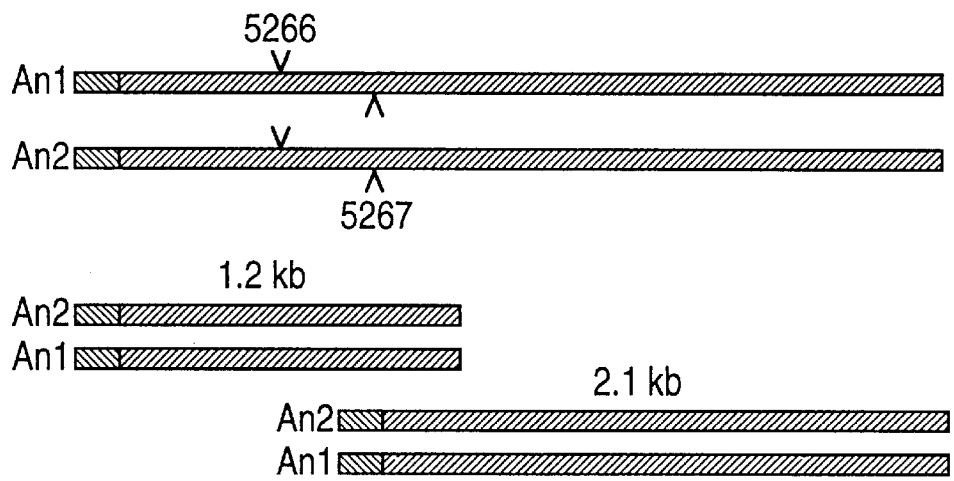

FIG. 8A

```
        →Anl Promoter
GAATTCTTTT  AAAAAAATAA  CGTCTGTGCC  TCACAGTAGC  TGTAGGAGTA  GGGTGTTGCA   60
TCTCGCGCTT  CAATTCGGTC  GACAGCGGCT  CCTGTGGTCT  CCAGCCTTTA  CCGCTTTGGC  120
AACTGGTTCT  GTTTCAATCA  GGTCCATGCC  GTATCTTGCT  AAAGCTAAAA  ATAAATGCGT  180
TCACGGGAAC  GGCGTGTGTC  CGTGTTTCTG  CTCTGCTGCA  TGCAGCTCTC  GCCTTTATTT  240
TTTCTTTCCA  TCAAAAGCAA  CCGATGACCA  ACGGCCTTAC  ACAGTCTGTC  GAGAACTCGA  300
GATTCTCCAT  CCCCCCAAAT  GAAAACGAGG  TCGTAAATCT  CGCTTCACGT  CGGTAAGTCT  360
AAAAAATCTT  AAATTTAACT  GAACTTGTTA  AAGATATTGT  CAACATTTAG  ATGTTTAGTT  420
AAATTTACTA  TAAAAAAAGT  ATCTTAAGAT  ACGTCCATTC  AGTAAAAAAA  AAACAAAAAG  480
AAAAACTTTA  ACTATTCGAC  AAACGAGATT  TTTTTTTCCC  GGGTTGCCGT  CCCACTGCAC  540
GGACTAGTTG  CCAGGCATCT  TCCCTGAAAC  AAAAAGGAAA  ACACCAGTTC  TAGGCACGTA  600
CGTACTACGC  TTACGTGTAT  ATAAATATTT  ATCGGCTGTG  GACAGATTAT  AGAGGGCATC  660
TTGTTGCGAC  GGGGCGACGA  ATGTCCGTCT  CCAGCCACCC  GTCCGTTCGC  AAATCACGTA  720
CAAAGCTACT  TTGTGTTAGC  AGAAAACAGA  TAAAAAACAA  AATAGATCAA  CTAACAAATC  780
TGGAAGCACG  ACACATAAAT  TTACTTAAAA  ACCTTTCAAT  GAGAAAGGAA  AAATTATGAG  840
CACCAGCCAG  TTGATGTGAA  GTGTTTATGT  AACGTCGTTC  GTAGACGGCG  GCTTACAAGA  900
GAAGTAAAAA  GACGACGTGC  GATAAATTCT  AATTAGGTTC  ATTAATATAT  ACCTAAGTTT  960
TTGGACGATG  GGTATCCACT  CTGCTCGCTA  ATATTGTCTC  TATATTCAGA  ATTTGGATCA  1020
CAAACTTAAT  AGTTTGGTTG  GTTATGTATA  CAGTATACTC  ACGCACCAAC  GCACGCACGC  1080
CGCGAGAAGG  ATTAGCGAAA  CGCTGGTGGT  TTTTTGTCCA  CTAGCCGGTG  CGTCCCCGCG  1140
CGGGAATCAT  TCGGGCCTGC  CTCTCTACTC  TGCTCCCAGC  TACTAGTCCC  TCACTCACTT  1200
CTCTCAGACT  TGTGTGTCTC  GTCCTATATA  TATATACACA  CGCTACGCTA  TAGCTGCTCA  1260
```

FIG. 8B

```
CACACATAGT ATCGTCGTCT CTCTCTCCTT CCCACCAACA ACGCACGCGT CGAAGAAGGA 1320
AATGATTAGT AGCAGCCATA CTTGCTCCGC CTATTAATAG CCAGCGCGCG CGTCTTGTTT 1380
TGCTCTCTTC TGTTCTGTTT TGCCCTAGAT TAGCGGCGGC GTTTTGGCCT CGCCGAACG  1440
TCTCGTCCTT GCCGTCTCGC GCGCGTGCGT ACGTGCCTGC ATTGCGATTT GCAATTATTA 1500
GCATCGCGCG GCGGGGCGG  GCCGCCCATG AAGCTCCTCT CGCCGGCGGC CGCACCGTCG 1560
TCCTCGCCGT TGTTCCCTCC TCGCATCGTC GAAGGTACGT GTACACCGTC GTCAGCAGCT 1620
GCTACCTCCG CGGCGCCGGC CAGCCGGAGGT TCCATGATGC CTATCTATCT ATGTATAGTA 1680
CGTATATGGC GCCGCGCCAG GCCCTTGCCC TTGTCGTCTG CCTGCATGCC TACTACTACA 1740
AGCTACTTCC AAATTTCGCA TTGTCCTCGG CGCTACACGG CCGGTGGGCA ATCAGACAAA 1800
GAAACAAACG TGTAAGCAAG ATGAAAAATT GTATTTTTGG GTTCGGACAA GCAAGTCGTC 1860
GTCGTCGTCT TAGGGTAGCC ACACACACAG GCAGATGGGC AATCAGACAA AGAAACAAAC 1920
ATAAGCAAGA TGGAGAGAGG CAGGCAGGCA GTCAGGCCGCT GCTGCTGCTA GTG        1980
```

PLANT GENES AFFECTING GIBBERELLIC ACID BIOSYNTHESIS

The present application is a continuation-in-part of application U.S. Ser. No. 08/261,465, filed Jun. 17, 1994 now U.S. Pat. No. 5,612,191.

BACKGROUND OF THE INVENTION

The present invention relates to genes encoding regulators of gibberellic acid biosynthesis in plants. Plant development is affected by alterations in the nature or quantity of expression products of these genes. A family of An genes, found in monocotyledonous plants (monocots), codes for a composition essential for the conversion of GGPP to ent-kaurene involved in the early steps of gibberellic acid (GA) biosynthesis. Illustrative members of the family, the genes Anther ear1 (An1) and Anther ear2 (An2) are identified in maize cloning and functional attributes of the An1 and An2 genes are described. An genes are also identified in barley, sorghum and wheat by their homology to the An1 gene of maize.

That GA is important in plant development is illustrated by the correlation between increased vigor in hybrid maize and higher GA levels compared to parental levels, and the greater response of inbreds (compared to hybrids) to exogenously applied GA content (Rood et al., 1988). Further, RFLP analysis points to known GA biosynthetic loci as quantitative trait loci (QTLs) for height in maize hybrids (Beavis et al., 1991), suggesting a role for GA in heterosis. The importance of GA in plant development is further evidenced in the phenotype of GA-deficient mutants of maize, which includes: reduced plant stature, due to shorter internode lengths; shorter broader leaves; less branching of the tassels; and the development of anthers on the normally pistillate ear, resulting in perfect flowers (Emerson and Emerson, 1922).

In maize and probably other plant species, the reduced stature is primarily the result of a decrease in the final length of shoot cells. A reduction in the number of cells per internode is also a factor. Although GA deficiency affects maize shoot and mesocotyl cell length, coleoptile cell lengths are unaffected, suggesting that coleoptile cell extension is independent of GA. The reduced plant height of GA deficient/responsive mutants of maize is a characteristic common to GA deficient/responsive mutants from a number of plant species including Arabidopsis, tomato, rice, pea, and barley. Interestingly, the reduced height phenotype appears to be more responsive to GA levels than the development of anthers on the ear. This is true because, despite the semi-dwarfed to non-dwarfed stature of An1 mutants, they remain anther-eared.

Gibberellic acid levels also affect fertility in plants. For example, GA can be sprayed directly on plants to affect fertility. The nature of the effect is species specific, that is, in some species excess GA enhances fertility; whereas, in other species, GA reduces fertility. The effect depends on the reproductive mechanics of the species, and on the structure or function affected by GA.

In maize, a monecious plant with diclinous flowers, staminate flowers form on the tassel, while pistillate flowers form on the ear. Maize ears arise from axillary buds. Protuberances develop in an acropetal gradient on the ear that bifurcates-becoming two lobed. However, the diclinous nature of the mature flowers belies the fact that all flowers in the tassel and ear are initially perfect. Very early during their development, differentiation of pistillate and the staminate structures is arrested in the tassel and ear, respectively (Cheng et al., 1983). Flowers, known as florets in maize, are paired in the ear. Each pair arises from bifurcation of a spikelet, with one floret proximal to the ear axis and the other distal. Development of staminate structures in the ear is arrested in both florets, as is development of the pistillate structure in the proximal floret. Thus, the ovule of the distal floret contains the only mature gametophyte found in the ear, and when the enclosed egg and polar nucleus are fertilized, they develop as a kernel. Florets in the anther arise in a similar fashion, with development of the pistillate structures of both florets arrested very early, while stamens develop in both florets.

Reduced GA levels affect the development of pistils and stamens in maize by arresting development of the stamens in both florets of the ear. This results in a staminate flower in the proximal floret and a mature perfect flower in the distal floret. The development of pistils and stamens in the tassel of GA deficient mutants is delayed, but otherwise is unaffected. Thus, GA is required for the normal arrested development of stamens observed in both florets of the ear. The proximal anthers on ears of GA deficient responsive mutants produce mature pollen that accumulates starch and possesses a germ pore; these are indications of a functional gametophyte. Sexual determination of tassel florets in these mutants appears to be normal, with both florets developing fertile anthers, while the pistillate structures fail to develop. The effect of these mutations on the tassels appears to be limited to reducing branching and causing a poor pollen shed apparently due to failure of the glumes to open.

In maize, tassels and shoots have served as sources for the identification of a number of GA biosynthetic intermediates (Suzuki et al., 1992; Hedden et al., 1982). In addition to being present in shoots, GAs have been shown to be present in root tips of Pisum (Coolbaugh, 1985) and in immature seeds of Pharbitis (Barendse et al., 1983).

Gibberellic acids are synthesized from the isoprenoid GGPP, beginning with the cyclizations of GGPP to CPP, then CPP to ent-kaurene, catalyzed by kaurene synthases A and B (previously kaurene synthetases A and B), respectively (Duncan et al., 1981). Most higher plants are thought to be like maize in that, in maize, ent-kaurene is oxidized stepwise to 7-hydroxy-kaurenoic acid, which is converted to the first true gibberellin; $GA_{12}$-aldehyde (Suzuki et al., 1992). The latter compound then is oxidized further to an active GA by one of three parallel pathways. In maize the dominant pathway appears to be the early 13-hydroxyl pathway (Hedden et al., 1982), with GA1 being the penultimate, active product, typically present in less than 1 μg/100 gfwt amounts (grows fresh weight of tissue) (Fujioka et al., 1988).

The biosynthetic block in four of the five documented GA-deficient mutants of maize has been predicted by measuring accumulation of endogenous GA biosynthetic intermediates, and measuring growth responses to, and determining the fate of, intermediates (Fujioka et al., 1988). The precise biosynthetic role of the fifth locus, An1, has remained undetermined heretofore. Mutations in An1 result in a GA-deficient phenotype, curable with applied ent-kaurene, which suggested that the An1 gene product functions in ent-kaurene synthesis. However, An genes have not been cloned, isolated or sequenced. Therefore, genetic engineering methods for manipulating An genes to control plants are not available in the art. The availability of genetic engineering for GA levels would accelerate and enhance previously available classic breeding programs.

Genes have been cloned from maize using the Mutator transposable element family (Mu) to generate gene tagged mutants. Among the genes thus cloned are a1 (O'Reilly et al., 1985); bz2 (McLaughlin et al., 1987); hcf106 (Marteinssen et al., 1989); hm1 (Johal et al., 1992); iojap (Han et al., 1992); vp1 (McCarty et al., 1989) and y1 (Buckner et al., 1990). However, the use of the Mu system for cloning is not predictably successful.

SUMMARY OF THE INVENTION

Control of levels of gibberellic acid (GA) in plants by genetic engineering techniques requires identification and isolation of genes whose expression affects the operation of the biosynthetic pathway leading to gibberellic acids. Control of GA levels is a means of controlling plant development.

An aspect of the present invention is to identify, isolate and characterize a family of genes in monocots that is capable of encoding a product that functions to convert GGPP to ent-kaurene in gibberellic acid biosynthesis. As used herein, the term monocot includes sorghum, wheat, maize, and barley. The family of genes is defined by a capability to hybridize under conditions of high stringency with the An1 gene from maize, and therefore is designated "An". The genes of this family encode products that are necessary for the conversion of GGPP to ent-kaurene in the biosynthesis of gibberellic acid. Without being bound by theory, it is believed that the product is an isoprenoid cyclase. A representative member of the family is the Anther ear1 (An1) gene from *Zea mays*, which has been isolated, cloned, sequenced and characterized. The An1 gene is required for the accumulation of normal levels of GA in maize, and is understood to encode ent-kaurene synthase A, the enzyme involved in the first committed step of GA biosynthesis. Defective mutations of this gene cause the plants to be dwarfed, anther-eared and late-flowering.

Other members of the family of An genes of the present invention were located in barley, wheat and sorghum, by means of the ability of a candidate gene to hybridize with an oligonucleotide probe from a maize An1 gene nucleotide sequence of the present invention. Part of an An1 clone was used as a probe. Genomic DNA was extracted from barley, sorghum, and wheat plants. Each genus was analyzed separately. The genomic DNA was digested and separated by gel electrophoresis. The separated DNA was blotted. An An1 DNA probe was used to search for homologous nucleotide sequences in barley, sorghum and wheat. In addition, a maize An2 gene was detected in maize. Products of An2 mutant genes decrease GA levels, although to a lesser degree than effected by the An1 gene product. A double mutant plant, that is, a plant with a mutation in both An1 and An2, may be characterized by a more severe phenotype than either single mutant, that is, a severe dwarf phenotype.

DNA and RNA gel blot analysis demonstrate An1 to be a single copy gene. Sequence analysis of a 2.8 kb An1-cDNA clone shows homology with plant cyclase genes and a polyprenyl pyrophosphate binding domain. The initial steps in the GA biosynthetic pathway involve binding a polyprenyl pyrophosphorylated substrate, geranylgeranylpyrophosphate, which is converted by cyclization to kaurene, steps for which An1 plants are defective. Northern analysis of the An1 transcript indicates that it accumulates in shoots, roots, immature ears and kernels, silks and tassels. The transcript does not accumulate in dark grown shoots, suggesting that light is a regulator of An1 expression. Expression of An1 was monitored in a number of An1 isolates, as was its expression in maize shoots, roots, tassels, silks, pollen, and kernels. Light induction of An1 transcripts have been demonstrated in seedling shoots.

Cloning GA biosynthetic genes provides recombinant genetic tools leading to a better understanding of the role GA plays in the growth and development of maize. In addition, control over GA levels can be used to manipulate plant development by recombinant DNA technology to specific ends.

An1 is one of five identified genes in maize that are involved in GA biosynthesis. Mutants of all five genes (An1, d1, d2, d3, and d5) are anther-eared, but An1 is distinct from the others in that its stature is invariably semi-dwarfed rather than dwarfed. The semi-dwarfed stature appears to result from a redundancy in the maize genome for the An1 function. Evidence of this redundancy comes from an1-bz2-6923, a deletion mutant that lacks the An1 gene yet accumulates ent-kaurene, a downstream product of An1 activity. Further support for redundancy comes from low stringency Southern analysis of an1-bz2-6923 DNA which demonstrates the presence of sequences with some homology to An1. One of these sequences is identified as the An2 gene, the existence of which was not suspected from the classical breeding experiments which identified the other GA biosynthetic maize genes.

The An1 gene product is involved in kaurene synthesis, early in the gibberellic acid (GA) biosynthetic pathway. Thus, the loss of An1 function results in a GA-deficient phenotype that causes altered development including reduced plant height and the development of perfect flowers on normally pistillate ears. An An1 allele was generated by Mutator induced mutagenesis, and the gene was cloned using a DNA fragment that is common to both Mu1 and Mu2 as a mutant gene probe.

The An1 gene was cloned from maize using a mutant fragment as a gene probe. In a tagged An1 isolate, an1-891339, Mu2 is inserted in the coding region of the An1 gene. This results in a GA-deficient phenotype. The identity of the An1 clone was confirmed by a comparison of the predicted amino acid sequence with that of a GA1 gene from Arabidopsis (See PCT patent application WO/9316096). The two genes are 47% identical and 68% similar (GCG package, Genetics Computer, Inc., University of Wisconsin) at the amino acid level, suggesting that they have a common function.

An1 contains a polyprenylpyrophosphorylase binding domain and shares homology in this region with other plant cyclase genes. Southern analysis of a deletion mutant, an1-bz2-6923, demonstrated that the An1 coding region lies entirely within the deletion. But the deletion mutant accumulates kaurene, indicating that An1 function is partially supplemented by an additional activity. In fact, low stringency Southern analysis of deletion mutant DNA demonstrates the presence of DNA sequences homologous to An1, for example, the An2 gene, which was isolated by the RT-PCR method. Therefore, it is likely that the semi-dwarfed stature of An1 mutants, as opposed to the dwarfed stature of the other GA-deficient mutants in maize, is based on redundancy in this step of the GA-biosynthetic pathway. A double mutant, with deficiency in GA levels effected by more than one gene, may show a more severe phenotype than a single mutant.

Antibodies have been prepared to the An1 gene product. The antibodies coupled with in vivo and in vitro assays of kaurene synthase A and B activity from An1 constructs cloned into *E. coli* expression vectors allow the An1 gene product to be tested for kaurene synthase A and B activity. Complexes were formed with kaurene synthase A and the An1 clone gene product.

The identity of a second gene product that catalyzes the first committed step in the synthesis of the plant hormone gibberellic acid has been determined through the use of oligonucleotide primers derived from the An1 sequence. oligonucleotides homologous to the An1 nucleotide sequence were generated and used to synthesize a 485 bp RT-PCR fragment that is highly homologous to but distinct from An1, as evidenced by a restriction site analysis of a corresponding nucleotide stretch in An1. This fragment has been designated as An2. The resulting 485 bp RT-PCR product is used to derive An2 specific primers. These primers are used to isolate full length cDNAs of An2 and to determine its mRNA sequence.

Changes in plant developmental activity and yield have been accomplished in the past via conventional breeding, which requires an entire genome to be recombined, rather than a single gene or selected set of genes, and which is limited to natural genetic variability rather than being amenable to genetic engineering. The family of genes provided by the present invention permits engineered placement of such genes in a uniform background, for better control of plant developmental aspects such as stature and fertility, and manipulation of the genes per se to achieve specific plant breeding objectives. For example, adding An genes to a plant to increase GA levels or adding an antisense molecule to decrease GA levels.

Definitions

In the description that follows, a number of terms are used extensively. The following definitions are provided to facilitate understanding of the invention.

In eukaryotes, RNA polymerase II catalyzes the transcription of a structural gene to produce mRNA. A DNA molecule can be designed to contain an RNA polymerase II template in which the RNA transcript has a sequence that is complementary to that of a specific mRNA. The RNA transcript is termed an antisense RNA and a DNA sequence that encodes the antisense RNA is termed an antisense gene. Antisense RNA molecules are capable of binding to mRNA molecules, resulting in an inhibition of mRNA translation.

A cloning vector is a DNA molecule, such as a plasmid, cosmid, or bacteriophage that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

Exogenous denotes some item that is foreign to its surroundings, and particularly applies here to a class of genetic constructs that is not found in the normal genetic complement of the host plant. Thus, in the present invention an exogenous construct used to produce a plant via transformation includes an operative promoter and an isolated DNA molecule having a nucleotide sequence of a member of the family of genes of the present invention.

An expression vector is a DNA molecule comprising a gene that is expressed in a host cell. Typically, gene expression is placed under the control of certain regulatory elements, including constitutive or inducible promoters, tissue-specific regulatory elements and enhancers. Such a gene is said to be "operably linked to" the regulatory elements.

Heterologous is a modifier indicating a source that is different. For example, a heterologous promoter used with a structural gene of the present invention is a promoter that is different from that of the structural gene.

An isolated DNA molecule is a fragment of DNA that is not integrated in the genomic DNA of an organism. For example, the nucleotide sequence of the An1 gene is a DNA fragment that has been separated from the genomic DNA of a maize plant. Another example of an isolated DNA molecule is a chemically-synthesized DNA molecule that is not integrated in the genomic DNA of an organism.

Isolates are mutant plants derived from independent sources.

A recombinant host may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

RT-PCR is a method known to those of skill in the art. Components used herein for RT-PCR were obtained from GIBCO-BRL, Gaithersburg, Md. The manufacturer's instructions were followed.

Two nucleic acid molecules are considered to have a substantial sequence similarity if their nucleotide sequences share a similarity of at least 50%. Sequence similarity determinations can be performed, for example, using the FASTA program (Genetics Computer Group; Madison, Wis.). Alternatively, sequence similarity determinations can be performed using BLASTP (Basic Local Alignment Search Tool) of the Experimental GENIFO(R) BLAST Network Service. See Altschul et al., *J. Mol. Biol.* 215:403 (1990). Also, see Pasternak et al., "Sequence Similarity Searches, Multiple Sequence Alignments, and Molecular Tree Building," in Methods in Plant Molecular Biology and Biotechnology, Glick et al. (eds.), pages 251–267 (CRC Press, 1993).

A suitable promoter is a promoter that controls gene expression in cells that are to be altered developmentally by the manipulation of genes controlling biosynthesis of GA.

A transgenic plant is a plant having one or more plant cells that contain an expression vector.

BRIEF DESCRIPTION OF THE DRAWINGS

FIG. 2 is an amino acid sequence comparison between gene products of the maize An1 gene (top) (SEQ ID NO:5) and an Arabidopsis gene, GA1 (bottom) (SEQ ID NO:6).

FIGS. 3 A and B is the cDNA sequence of the An1 gene isolated from maize (Gen Bank accession number L37750) (SEQ ID NO:7).

FIG. 4 illustrates the role of gibberellic acid in maturity of maize by reference to a comparison of days required for maturity for an1-bz2-6923 and its wild-type siblings. GDUSHD is heat units to pollen shed, 25 units ~ 1 day.

FIG. 6 is a cDNA sequence of an An2 gene isolated from maize (SEQ ID NO:8) aligned with a fragment of a corresponding segment of the An1 gene nucleotide sequence illustrated in FIG. 3 (bases 710–1259 of SEQ ID NO:7).

FIG. 7 is a restriction site map of the corresponding nucleotide sequences of An1 and An2 according to FIG. 6.

FIGS. 8 A and B is a nucleotide sequence (SEQ ID NO:9) of the promoter of the An1 nucleotide sequence of FIG. 3. Position 7 on FIG. 8A is the beginning of the promoter.

DETAILED DESCRIPTION OF THE PREFERRED EMBODIMENT

Gibberellic acid (GA) levels are important factors in plant development. Control of GA levels by genetic engineering technology allows alteration of plant phenotypes such as fertility and size. Identification and isolation of genes controlling the biosynthesis of GA are required for this effort. A family of genes has been identified that is capable of encoding a product that is necessary for the conversion of GGPP to ent-kaurene in the biosynthesis of gibberellic acid. The product is consistent in structure with a cyclase. Members of this gene family hybridize with the An1 gene under conditions of high stringency. These genes also encode products that are the functional equivalent of the sequence in FIG. 2 (SEQ ID NO:5) within the box. FIG. 2 shows the correlation between the predicted amino acid sequence of An1 (top) (SEQ ID NO:5) and that of GA1 (bottom) (SEQ ID NO:6).

Figure 1A:
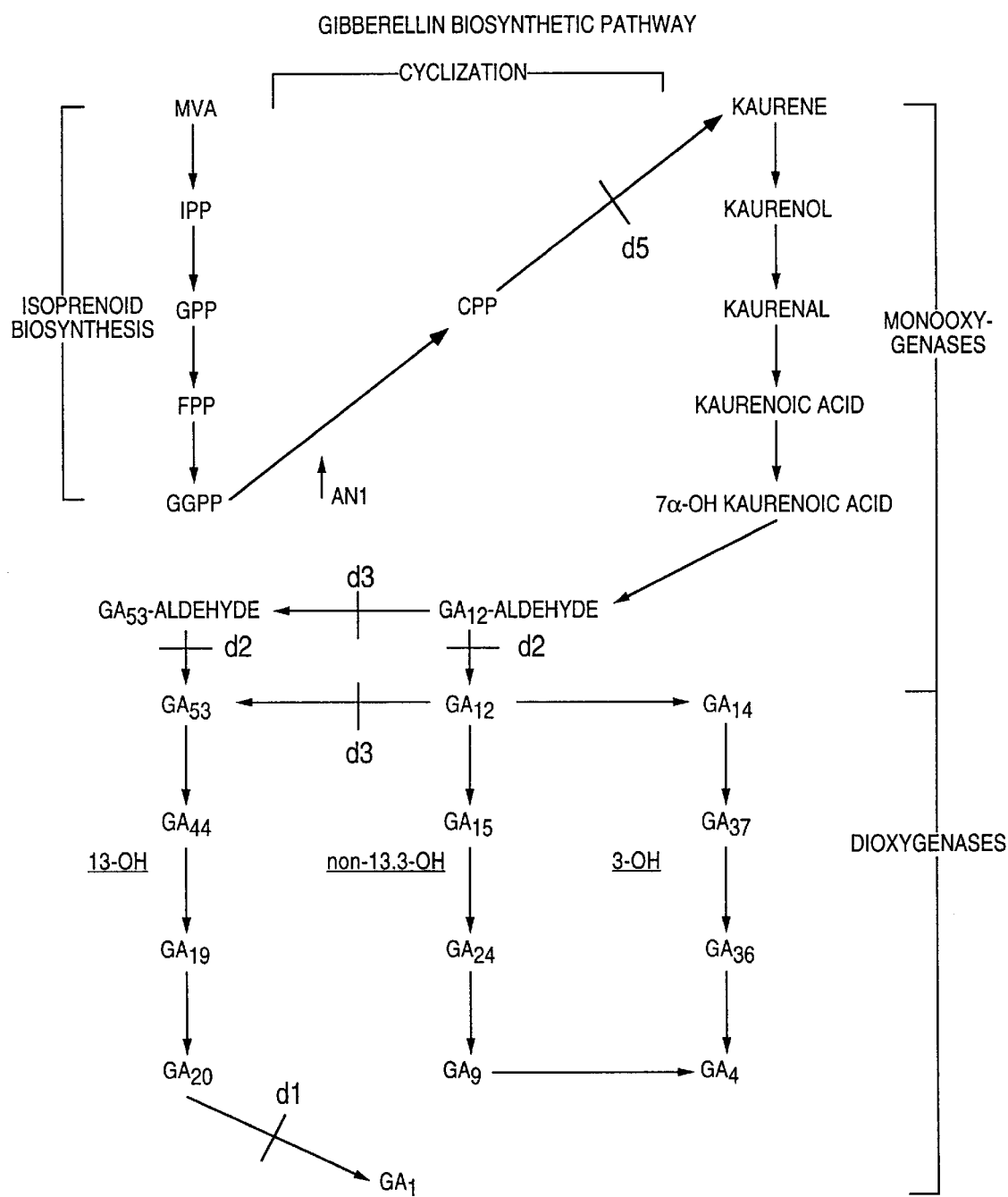
FIG. 1A is a schematic representation of the GA biosynthesis steps and FIG. 1B focuses on steps catalyzed by kaurene synthetase A and B.
Figure 1B:
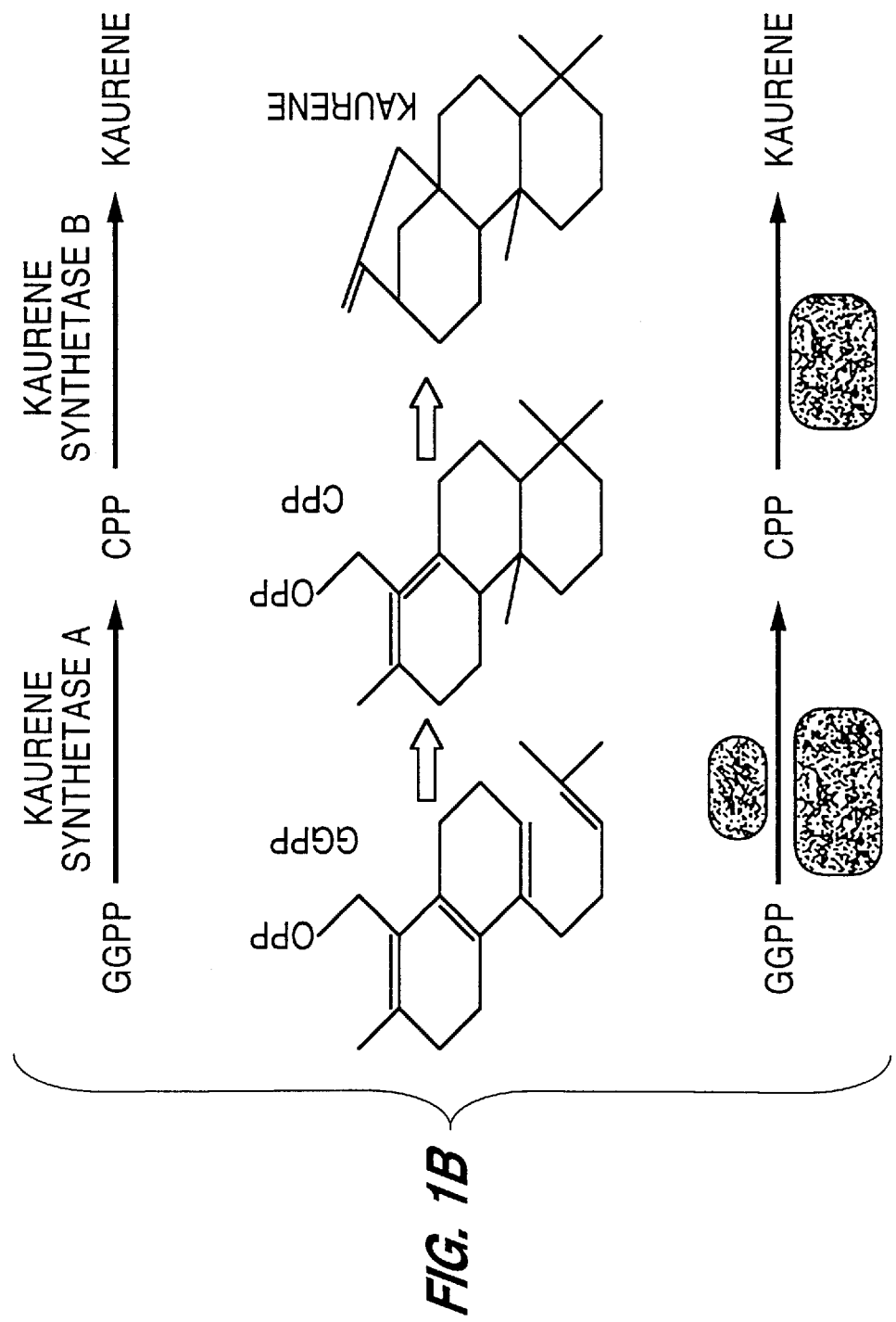

Steps catalyzed by kaurene synthase are as follows: Two rings are closed in the conversion of GGPP to CPP by kaurene synthase A. The third ring is closed, the pyrophosphate group is cleaved, and a carbon-carbon bond is broken and reformed at a nearby site as CPP is converted to ent-kaurene by kaurene synthase B (FIG. 1B).

Also as noted, An1 is one of five identified genes in maize that are involved in GA biosynthesis. The An1, d1, d2, d3, and d5 mutants of maize compose a class of recessive mutants that are GA deficient and GA responsive. They all appear to be defective in some step of the GA biosynthetic pathway, and they share a number of phenotypes, including reduced stature and the development of anthers on the normally pistillate ear.

Within this class of mutants there are two distinct groups relative to stature. Alleles of d1, d2, d3, and d5 are typically severe dwarfs, exhibiting an 80% or greater reduction in final plant height. In contrast, alleles of An1 are less severely dwarfed, typically semi-dwarfed, and in some cases there is no reduction in their final height. The severity of reduction in shoot height for both groups is also reflected in the degree of reduction in their leaf lengths. For the entire class the reduction in height is scorable in both light and dark grown seedlings. In six day-old dark grown An1 seedlings, the basis of the reduced height lies in the cells of the mesocotyl. Coleoptile cell number is slightly reduced in An1 seedlings, while the average cell length of coleoptile cells is the same as found in wild-type siblings (Table 1). This is in contrast to the mesocotyl where cell number is reduced by one-half and average cell length is reduced to one-fourth of that observed in wild-type seedlings. Thus, the reduced stature in dark grown seedlings is due primarily to greatly reduced final cell lengths.

TABLE 1

Comparison of Cell Length and Cell Number in Shoots of Dark Grown Maize Seedlings.

|  | Length (mm) | Number of Cells | Average Cell Length(mm) |
|---|---|---|---|
| Tall Sibling |  |  |  |
| Coleoptile | 18 | 228 | 0.08 |
| Mesocotyl | 70 | 294 | 0.18 |
| Total | 88 | 522 |  |
| Dwarf (An1) |  |  |  |
| Coleoptile | 14 | 171 | 0.08 |
| Mesocotyl | 6 | 130 | 0.05 |
| Total | 20 | 301 |  |

The An1 gene was cloned using transposon tagging. A key advantage for tagging genes with mutator is the 50-fold or greater increase in mutation frequency compared to spontaneous rates. See Walbot, 1992 for a review. Transposon tagging involves using any one of a number of naturally occurring plant transposons—Mu, Ac, Spm and the like—to create a "molecular tag" to recover the mutated gene. Although it has been used before, the transposon-tagging approach to recovering a gene of interest is unpredictable, is plagued by a low mutation frequency, and is very difficult technically. First, the genetic stocks have to be screened phenotypically for mutants of interest. There is no way to direct the transposon to a particular gene or to produce a particular phenotype. After a mutant phenotype of interest is found, moreover, it is necessary to determine whether the mutant is actually caused by the insertion of a transposon, because not all mutations are caused by transposable elements. A gene can be isolated by transposon tagging only if a particular transposon has inserted into the gene.

Each transposon system has major advantages and disadvantages. Ac and Spm, for example, occur in lower copy number per genome than Mu and therefore promote a lower frequency of mutations. Because both of these elements excise from the germline at a higher frequency than Mu, however, it is possible to use the powerful genetic tool of looking for a reversion of the mutant phenotype as a result of excision of the element from the germline. This provides very strong evidence that a particular mutant was caused by the transposon insertion. Mu has the advantage of having a high copy number, so the frequency of causing mutations is higher (up to 10–100× higher than the background mutation rate). Because the germline excision frequency is very low (~1 in 10,000), however, standard tests for reversion are not practical. Other, labor-intensive means need to be used to prove that the gene is tagged by the transposon. Those methods are molecular detection methods which involve isolating DNA from the mutant plants of interest, and probing the DNA for the presence of a Mu element which co-segregates with the mutant phenotype. With Mu this is particularly difficult, because there are many copies of Mu per genome—in fact, some genomes have over 200 copies (Walbot and Warren, 1988).

For the present invention, co-segregation of an an1-891339 phenotype and Mu2 containing restriction fragments was demonstrated by Southern Blot Analysis. DNA from individual homozygous F2 dwarfed an1-891339 siblings was analyzed to determine linkage between the mutation and a Mu element. DNA was restricted with SstI, and the blot was probed with an internal Mu2-DNA fragment. A Mu2 containing restriction fragment of 5.7 kb, common to all tested individuals, was identified. This Mu2 containing restriction fragment was cloned into a lambda vector. DNA gel blot analysis of a restriction digest of the clone was performed. Double digests of the cloned fragment was in Lane 2 (SstI and HindIII) and Lane 3 (SstI and XbaI).

Flanking sequence DNA was identified, and a 2.6 kb flanking sequence fragment (g2.6Xba) was subcloned and used as a probe. Southern blot analysis of the deletion mutant (an1-bz2-6923) was performed as follows:

Southern blots of SstI digested genomic DNA of the deletion mutant and wild-type sibling DNA were analyzed. A blot probed with genomic flanking sequence subclone g2.6Xba showed deletion mutant plants lack DNA homologous to g2.6Xba. Using g2.6Xba as a probe, a 2.8-kb cDNA clone was recovered from a maize cDNA library. This cDNA appears to represent full-length mRNA based on RNA gel blot analysis: the primary product is a homologous transcript of a 2.8-kb. The cDNA contains an open reading frame of 2.5 kb or 823 amino acids, as illustrated in FIG. 3 (SEQ ID NO:7).

A sequence comparison of maize An1 and Arabidopsis GA1 showed the complete predicted amino acid sequences of An1 and GA1 are similar. Overall identity is 47%, similarity 68% (GCG package, Genetics Computer, Inc., University of Wisconsin). A putative polyprenylpyrophosphorylate binding domain is indicated with a box (FIG. 2).

The homology between predicted amino acid sequences of maize An1 (SEQ ID NO:5) and Arabidopsis GA1 (SEQ ID NO:6) points to a common function for these genes. Their overall identity of 47% (68% similarity) is striking, but is even stronger in an internal 300 amino acid segment that is 68% identical (94% similar). As to the putative polyprenyl-pyrophosphate binding domain within this segment, An1and GA1 share 100% similarity. Other sequenced plant genes that use polyprenylpyrophosphorylated substrates (geranyl-, farnysyl- and geranylgeranyl-pyrophosphate) also share significant homology with An1 in this domain (Facchini et al., 1992), but much less overall homology with An1 (20 to 25% identity). These sequence homologies clearly indicate that An1 encodes a cyclase which functions in the conversion of GGPP to ent-kaurene.

While highly homologous to GA1, it is important to note that An1 is distinct from GA1 in its amino (only 11% identical for first 100 amino acids) and carboxyl terminus (only 18% identical for the last 283 amino acids). Also, the amino terminus of An1 has characteristics expected of a chloroplast targeting sequence including a net positive charge (12 of 43 amino acids are basic while only two are acidic). In addition, the An1 amino terminus also has a greater than 50% similarity to the amino terminus of an aspartate aminotransferase cDNA clone from rice (Gene Bank Source D16340). Aspartate aminotransferase has many isoforms, at least one of which is located in the chloroplast (Matthews et al., 1993). This suggests that the amino terminus of An1 serves as a chloroplast-targeting sequence. Support for a chloroplastic localization of kaurene synthesis comes from the demonstration that cell free assays of purified chloroplasts synthesize kaurene (Simcox et al., 1975). If An1 and GA1 code for the same chloroplast targeted activity, their targeting sequences are distinct. The low homology between An1 and GA1 in their carboxyl termini may be functionally important. While a number of plant cyclase activities share a conserved polyprenylpyrophosphate binding domain, they act on distinct substrates and cyclize by distinct mechanisms. The basis for these differences is not obvious from an examination of the primary amino acid sequences.

Southern blot analysis using high and low stringency was performed. Southern blots of homozygous deletion an1-bz2-6923 and wild-type sibling DNA compared from high (at a temperature of 65° C.) and low (at a temperature of 25° C.) stringency washes were compared. Genomic DNAs were digested with BamHI. The probe was An1-cDNA. Therefore, at high stringency, probe DNA hybridizes only to wheat and tall sibling DNA, whereas, at low stringency, hybridization occurs with deletion mutant maize. A related sequence is likely in wheat.

Northern blot analysis shows An1 transcript accumulation. Northern blots from total RNA preparations were probed with An1-cDNA. Tissues analyzed were:

(A) shoots and roots of light and dark grown seedlings; and
(B) reproductive structures.

The blot revealed An1 transcript accumulation in all tissues and an enhancement of accumulation in light grown shoots.

Since GA plays important developmental roles, its control is a useful avenue to altering development for specific purposes. The an1-bz2-6923 allele of An1 is consistent with a robust plant which demonstrates little or no reduction in plant height or leaf length compared to wild-type siblings. Despite its similarity in growth, the average first day of pollen shed in this mutant is delayed, in the example shown this delay is 5 days (FIG. 4). This demonstrates that lowering GA levels reduces time-to-maturity in maize, possibly by shortening the time required between germination and floral initiation.

A comparison of days required to maturity for an1-bz2-6923 and its wild-type siblings is shown in FIG. 4 as a plot of the height of wild-type siblings and an1-bz2-6923 mutants versus GDUSHD (heat units to pollen shed, 25 units≈1 day). Although no difference in final height exists, there is an average of 200 GDUSHDs delay for the mutant plants. Shortened time to maturity is an advantage in some growing zones (climates); whereas, increased time to maturity is an advantage in other growth zones. Therefore, the ability to manipulate GA levels by recombinant techniques is advantageous for developing commercial monocots. Isolation of genes such as An1 provides some of the tools needed for this endeavor. The An1 gene will also be useful to probe for homologous genes in other species. A gene homologous to An1 was isolated by RT-PCR. Construction of the primers used to generate the 485 bp RT-PCR product was completely dependent upon the previously determined An1 cDNA sequence as shown in by Bensen et al. (1995). Further oligonucleotide primers were generated from the 485 bp RT-PCR product.

Primers that are specific for An2 are used in a reverse genetics screen. A collection of corn families is used that has a high frequency and, perhaps many mutations. The large number of families is screened in sets of about 50 for gene mutations in areas of interest. PCR primers are defined for the mutator elements. Primers from the An2 fragment are matched to those in the families to detect specific families that have Mu inserted near the tested primer product of interest. Such families are then used for various breeding crosses. Plant families selected by this screen have Mu insertions in the An2 gene. Seed from progeny $F_2$ plant families are grown. No dwarfing phenotype is likely for these families, because An2 mutants only have 20% reduced levels of GA. However, crosses between these families and An1 mutant plants produce double mutants which are severely dwarfed, because both a 20% and an 80% decrease are combined. Alternatively, if An1 and An2 are different, complementation occurs.

The present invention is illustrated in further detail in the following examples. These examples are included for explanatory purposes and should not be considered to limit the invention.

EXAMPLE 1

Cloning the An1 Gene

Reports in the literature suggest that GA levels may be a partial cause of heterosis. To develop transgenic tools for improving yield in crop plants using genes affecting GA synthesis, a goal was to clone genes which encode enzymes of the GA biosynthetic pathway.

Several GA-deficient mutants of maize had been described (d1, d2, d3, d5, An1) which were associated with a dwarf stature and andromonoecious flowering (perfect flowers on the ear). If these mutations actually occurred in the genes directly coding for GA biosynthetic enzymes, it was difficult to envision how to identify and isolate the genes without having to purify the as yet uncharacterized enzymes in the GA pathway. One possible approach was to use transposon tagging, which had been successfully used in some cases to tag and isolate genes (Walbot, 1992). But dwarfs are very rare and, moreover, no known transposon-induced alleles had previously been reported for any dwarf mutants. An anther ear (An1) mutation segregating in a Mu-containing maize line was obtained from Patrick Schnable (Iowa State University), and experiments were carried out to determine whether a transposable element could be found associated with the mutant gene. The likelihood of this was questionable, however, because such transposon-tagged dwarf mutants had never been identified before.

The employed mutant-detection method involved isolating DNA from the mutant plants of interest and then probing the DNA for the presence of a Mu element which co-segregates with the mutant phenotype. This was particularly difficult because there are many copies of Mu per genome; in fact, some genomes have over 200 copies (Walbot and Warren, 1988).

In order to reduce the extremely large number of Mu-hybridizing bands, it was first necessary to make repeated crosses to plants that inactivated and diluted out most of the Mu elements. It was also necessary for the An1 mutant gene search to use Southern blots to probe genomic DNA separately with a DNA fragment that is unique to each of nine distinct Mu families. Even then, the number of copies per Mu family is around 25, making it very difficult to identify one hybridizing band in the blot that co-segregates with the Mu element used as probe. In doing such a DNA screen for An1, it was necessary to prepare DNA from 50 different individual plants and probe each of those samples in a Southern blot with each of the Mu-specific probes, Mu1, Mu2 and Mu3, that are characteristic of the sub-family.

After a Mu-tagged, co-segregating restriction fragment was found, the fragment was isolated by cloning and sequenced to identify the location of the Mu insertion. The flanking regions were also sequenced, to locate the structural gene of interest. For a gene like An1, not identified or isolated previously and, hence, of unknown sequence, it can be very difficult to determine the exact limits of the gene and even to prove that the clone contains the mutant gene of interest. As Walbot indicates in her 1992 review of strategies for mutagenesis and gene cloning using transposon tagging, identification of a co-segregating band is not straightforward. Moreover, identification of such a band is not proof that the band in question defines the gene of interest.

A family with a phenotype characteristic of GA deficiency was observed to segregate as a simple recessive trait in an active Mu line. The mutation was shown to be allelic with An1, and was identified as an1-891339.

Southern analysis of SstI-restricted genomic DNA from an1-891339 and its wild type siblings identified a Mu2-containing restriction fragment, of approximately 5.4 kb, which co-segregated with the mutation. This fragment was eluted from a preparative agarose gel, cloned into a bacteriophage lambda vector and plaque purified using a Mu2 internal fragment as a probe. Analysis of the cloned fragment, by restriction with XbaI or HindIII, identified fragments of flanking sequence DNA. A 2.6 kb XbaI flanking sequence fragment (g2.6Xba) was subcloned into a plasmid and used as a probe for Southerns and screening maize cDNA libraries. Southern analysis of maize genomic DNA demonstrated that g2.6Xba was single copy DNA.

Using g2.6Xba as a probe, a number of cDNA clones were selected from maize cDNA libraries, demonstrating that g2.6Xba lies in a transcribed region of the genome. The frequency of positive clones in each of two amplified libraries was 8 per 360,000 plaques. The longest of the cDNAs, 2.8 kb, was subcloned into a plasmid and sequenced. This cDNA appears to represent full length mRNA.

Comparing cDNA and An1 genomic DNA sequence identifies a number of exons. The comparison also demonstrates that the Mu2 element causing the mutation is inserted within or at the border of an intron, 1.6 kbp from the carboxyl terminal of the transcript and 900 bp from the amino terminal.

It was necessary to take several approaches to confirm the identity of the putative clone of the An1 gene. Tight linkage between the clone and the gene needed to be established by testing to show that the clone did not hybridize to DNA from a known genetic deletion mutant of An1. This evidence placed the clone to within a few map units (4 centimorgans) of the genetic locus for An1, based on the resolution of this mapping experiment. That distance corresponds to ~8.4 Mb×$10^6$ bp, so it is possible the clone could have been located as far away as 8.4 mb from the genetic locus for An1.

The next step was to isolate and sequence a cDNA clone. To do this, it was necessary to determine where the putative An1 gene was expressed so that a cDNA library could be created that was likely to contain the gene. Because the size of the mRNA was known to be quite large (~3 kb), recovery of a full-length clone was very difficult.

The first clone was only 2.5 kb in size, so it was necessary to screen a second library to recover a longer clone of 2.8 kb. The sequence of the cDNA showed ~40% similarity in only one region of the clone to an isoprenoid cyclase type of binding region, based on other known cyclase-type genes.

The biochemical function of An1 is known to be required for kaurene accumulation and is likely the cyclase which converts GGPP to CPP. This is known to be the first committed step in GA biosynthesis (kaurene synthase A).

Homology with other cyclases was consistent with one of the possible functions for the An1 gene product. The homology that was seen was very limited and far less than the overall homology typically seen among cyclases, so only tentative conclusions could be drawn as to the identity of the isolated gene. Therefore, additional evidence had to be obtained from other technical approaches.

Peptides were synthesized that corresponded to predicted antigenic domains of the protein which was encoded by the clone. Antibodies were raised against several peptides. Only 2 of the 4 antibody preparations were usable. Some of the antibodies were shown to precipitate the GGPP-to-CPP cyclase activity of cucurbit endosperm extracts, providing additional evidence to support the possibility that the isolated gene was An1. Finally, a comparison of amino acid sequence between our clone and a GA1 clone from Arabidopsis revealed significant homology throughout the length of the protein. GA1 has been shown to encode the GGPP-to-CPP cyclase (Tai-Ping Sun et al., personal communication).

These data provide a convincing case that An1 was cloned, but clearly, the process was a difficult and uncertain one. Although transposon tagging made it possible to clone the An1 gene, success was far from predictable.

The efficiency of obtaining an insertional mutant depends on a variety of factors, including the activity phase of the autonomous element(s), the number of mobile elements, the location of the elements and the susceptibility of the target locus (Walbot, 1992). As Walbot states in her review, "Although not often reported, some targeted mutagenesis screens fail completely, despite reasonable progeny sizes". Table 2 in her review indicates a number of examples where attempts to target specific genes by transposon insertion have failed. Based on the previous failure to identify any dwarf mutants which were transposon-tagged, it was not unreasonable to assume that the target locus for genes in the GA pathway might not be susceptible to tagging. Therefore, it was very uncertain that the An1 mutant from the Mu genetic stocks was in fact tagged by Mu. However, the An1 gene has been cloned, as shown herein.

EXAMPLE 2

Basis for Semi-Dwarfed Nature of An1 Plants

As described previously, An1 is unlike the other GA deficient/responsive mutants of maize in that it is a semi-dwarf. This is true of all four isolates of An1 examined. An1 plants respond to the application of a number of GA biosynthetic intermediates, including ent-kaurene. Since GA biosynthesis is initiated by the conversion of GGPP to CPP, followed by the conversion of CPP to ent-kaurene, An1 appears to be deficient in the conversion of GGPP to ent-kaurene.

Probing an1-bz2-6923 DNA on a Southern blot with either g2.6Xba or full length An1-cDNA resulted in no detectable hybridization of probe. Similar results were observed on northern blots of deletion mutant RNA. This indicates that the transcript of the An1 gene lies entirely within the deletion and is therefore not present in an1-bz2-6923 plants.

It would be expected, therefore, that this mutant would be absolutely defective in ent-kaurene synthesis. Yet light-grown an1-bz2-6923 seedlings accumulate ent-kaurene in vivo, albeit at a much reduced rate (20%) compared to their wild-type siblings (Table 2). This activity is attributed to the An2 gene product, a non-An1 activity that supplements An1 production of ent-kaurene. The supplementary activity is thought not to be unique to maize. A deletion mutant of Arabidopsis, GA1-3, also is expected to be devoid of ent-kaurene, since the GA1 coding region is entirely deleted (Tai-Ping Sun et al., 1992). However, GA1-3 plants convert GGPP to CPP and CPP to ent-kaurene in cell-free extracts of siliques. Notably, there are a number of GA1 isolates that demonstrate a uniform but variable reduction in plant height similar to that observed for the An1 isolates in maize. The accumulation of ent-kaurene is not observed in maize d5 mutants, however. The d5 mutant is believed to be defective in kaurene synthetase B as is the GA2 mutant of Arabidopsis which has A, but no B activity in cell free extracts from immature siliques. When the stringency of Southerns is lowered for blots of restricted an1-bz2-6923 DNA, by altering temperatures, bands sharing homology to An1 can be identified suggesting that homologous sequences provide An1 functional equivalents.

Thus, the consistent "leaky" or semi-dwarfed phenotype observed for all documented An1 mutants in maize is likely the result of a redundancy for An1 function. This redundancy does not exist, or is of little significance, for the kaurene synthetase B-encoding maize d5 and Arabidopsis GA2 genes, since their block in kaurene synthesis seems complete.

EXAMPLE 3

An1 Transcript Distribution and Expression

Transcription of the An1 gene in maize occurs in a number of tissues, as demonstrated by northern blots. Vegetative parts of the plant, shoots and roots, contain An1 mRNA. Reproductive tissues including tassels, developing ears, silks and embryos all contain An1 mRNA. Interestingly, etiolated shoot tissue appears to have very little if any An1 mRNA compared to light- grown shoots. The presence of message in the roots decouples this light-induced transcription from dependence on chloroplast development.

Using An1- specific primers derived from the An1 cDNA sequence, both qualitative and quantitative measurements of An1 transcript were made. The primers used were: 5'-TTGCCAAGCTCTGCATCAGCTTGAGTGT-3' SEQ ID NO:1 as a forward primer, and 5'-GGAAACATGTCTATCGATCATATGTTGTGGGGA-3' SEQ ID NO:2 as a reverse primer. By reverse transcriptase polymerase chain reaction (RT-PCR), using these primers, the distribution of An1 transcript in maize was determined to include: shoots, roots, silks, pollen, and tassels. Quantitative (Q-)RT-PCR using a competitive template (an An1 cDNA subclone with a 120 bp λ insert), it was determined that An1 transcripts accumulate upon exposure to light in maize shoots. Therefore, An1 transcript accumulation is induced by light. By the same Q-RT-PCR approach An1 transcript accumulation was shown to be repressed by GA treatment of plants.

EXAMPLE 4

Cloning An2 by RT-PCR

A deletion mutant in maize, designated an1-bz2-6923, produces 20% of the wild-type amount of biosynthetic product of the An1 gene. This production occurs despite the fact that the deletion mutant totally lacks An1 transcript and there is no evidence of genomic An1 DNA. Therefore, it was believed that the An1 gene has a functional homologue that catalyzes the production of the 20% residual activity. A priori this functional homologue could, be but is not necessarily homologous to An1. To locate the structural homologue to An1, a large number of primers to An1 were generated and tested by RT-PCR to see if any produced a PCR product using RNA isolated from the deletion mutant. Based on the lack of An1 DNA in the deletion mutant, RT-PCR products thus derived were used. One primer pair yielded an RT-PCR product. That primer pair was 5'CTTCGAGATCGCCTTCCCTTCTCTCA-3' SEQ ID NO:3 (5266) as the forward primer, and 5'-TAGCCCAGCAAATCCCATCTTCAGTCCA-3' SEQ ID NO:4 (5267) as the reverse primer. This primer pair produced a 488 bp product that was subcloned and sequenced. The nucleotide sequence (SEQ ID NO:8) was 82% identical to a portion of An1 (bases 710–1259 of SEQ ID NO:7). as aligned in FIG. 6. The predicted amino acid level was 82% identical and 91% similar to that of An1. This very high percent of homology suggested that An2 is a functional duplicate of An1.

EXAMPLE 5

Distinguishing An1 from An2

In the 488 bp region of interest, An1 and An2 each have unique PstI sites which allow the two genes to be distinguished when analyzing PCR products, cDNA libraries, or selecting a colony. The PstI polymorphism was used to screen libraries for the presence of An2. The presence of both genes in a maize seedling library resulted in the four band PstI digest pattern shown in FIG. 7. The top and bottom bands are attributable to An1, and the middle two bands are attributable to An2. The original primers, #5266 and #5267, were paired with primers homologous to "anchor" sequences located at the 5' and 3' ends of a seedling cDNA library that was shown to contain An1 and An2, and entire An1 and An2 cDNAs were generated by PCR as two fragments, sized 1.2 and 2.1 kb. Subcloning and transformation of these fragments into competent cells was followed by analysis of plasmid preparations from individual clones. PstI digestion of plasmid preparations revealed An2 cDNA clones for both the 1.2 and 2.1 fragments.

EXAMPLE 6

Use of Recombinant Genetic Methods to Affect Plant Development

Figure 5:
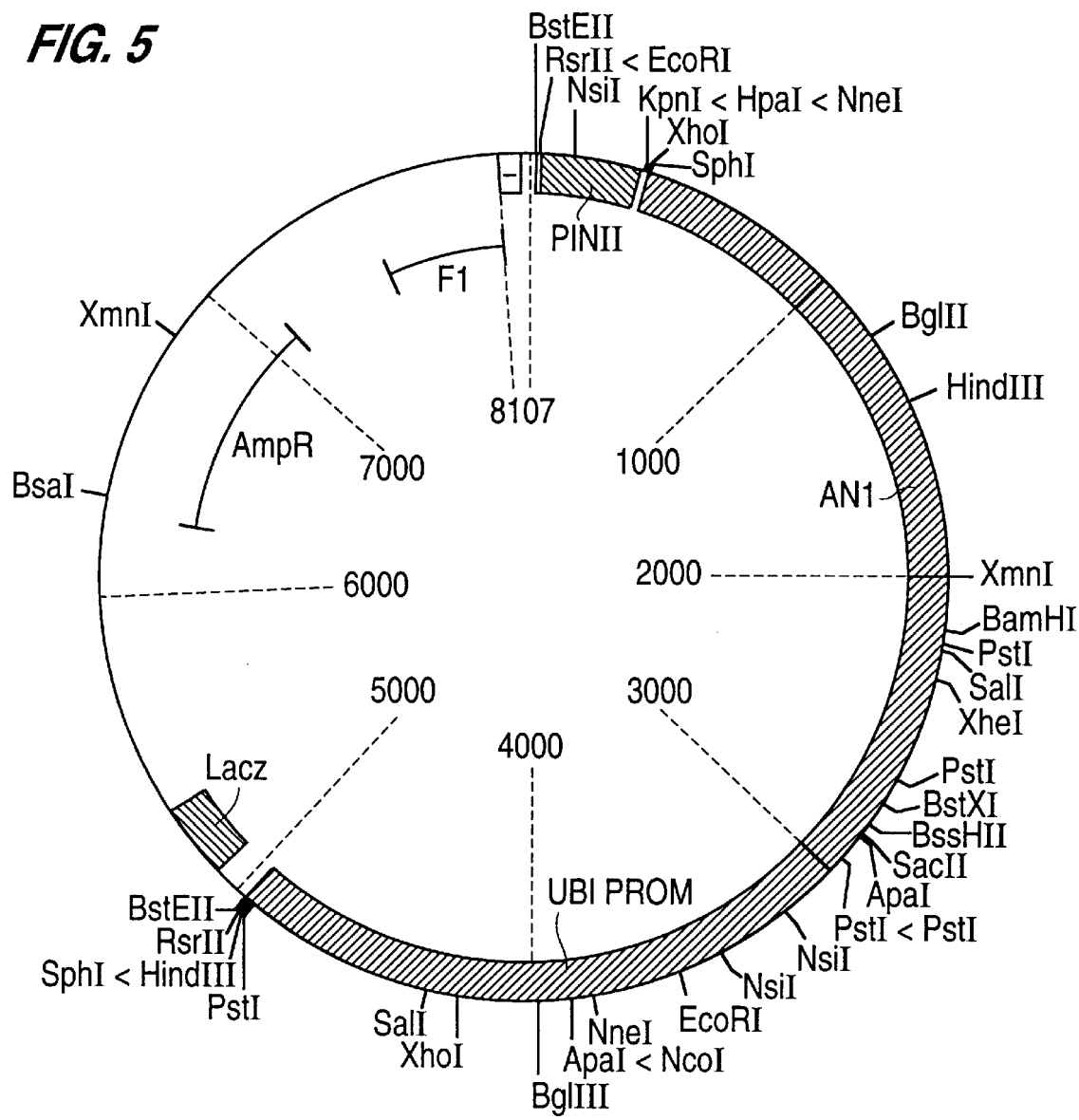
FIG. 5 is a plasmid map of DP6464.

Recombinant genetic methods make use of an isolated DNA molecule encoding a gene product which is necessary to convert GGPP to ent-kaurene in the biosynthesis of GA. The isolated DNA molecule is incorporated into a plasmid, such as that shown in FIG. 5, and transferred into a host plant. The expression of the DNA in the host will generally increase the endogenous levels of GA. The effect will depend on the species and the increment in GA levels. As shown herein, an mutations can affect time to maturity.

A strong, constitutive promoter is generally preferred to regulate a gene of the present invention in a host cell. Examples of suitable promoters are ubiquitin and 35S.

Decreasing endogenous GA levels is achieved by introducing an antisense molecule to a gene product of the present invention. Knowledge of the binding domain sequence (FIG. 2) allows such antisense molecules to be specifically constructed.

Directed mutation is useful to change a phenotypic gene of the present invention so that GA levels are reduced. The effects of reduced GA levels have been described above. Knowledge of a sequence of a maize An1 and a partial sequence of a maize An2 gene will facilitate targeted, site specific mutations not only in maize, but in other monocots which as described herein have homologues to An1 of maize.

TABLE 2

Kaurene Accumulation in Shoots of Light Grown Maize Seedlings.

| | Ent-Kaurene Content (pmoles/gfwt) | | Leaf Length (mm) | |
|---|---|---|---|---|
| | No | | | |
| Plant | Treatment | 48 h Tetcyclacis | 2nd Leaf | 3rd Leaf |
| an1-b2-6923 | | | | |
| Tall | 120 | 1330 | 42 | 83 |
| Dwarf an1-891339 | 33 | 209 | 30 | 58 |
| Tall | 61 | 710 | | |

TABLE 2-continued

Kaurene Accumulation in Shoots of Light Grown Maize Seedlings.

| | Ent-Kaurene Content (pmoles/gfwt) | | Leaf Length (mm) | |
|---|---|---|---|---|
| | No | | | |
| Plant | Treatment | 48 h Tetcyclacis | 2nd Leaf | 3rd Leaf |
| Dwarf d5 | 54 | 216 | | |
| Dwarf B73 | not detected 94 | not detected 1093 | | |

Seedlings were grown in continuous light for six days, at which time mM tetcyclacis (an inhibitor of kaurene metabolism) was applied directly to the shoots. Forty-eight hours later, the shoots of treated and non-treated plants were analyzed for ent-kaurene content.

EXAMPLE 7

An1 Promoter-GUS Fusion Constructs and Expression

Two thousand bases immediately 5' to the An1 start of transcription (i.e. the An1 promoter) have been cloned and sequenced. The sequence is shown in FIGS. 8A and B (SEQ ID NO:9). This 2 kb promoter region was fused to GUS. Transient expression assays on germinating seedlings demonstrated that the An1 promoter is sufficient for expression of the GUS fusion protein in roots and shoots.

METHODS

Plant Material

A Mu2 tagged An1 maize family, an1-891339, was selected from lines with active Mu elements (lines originated from Pat Schnable, Iowa State University). Additional An1 alleles used in this study include; an1bm2 (110D, Maize Genetics Cooperation Stock Center, U.Illinois), idd*-2286A and an1-bz2-6923 (both from G. Neuffer, U.Missouri). idd*-2286A is mutated in both the indeterminate locus (id) and the An1 locus (d) but does not appear to be a deletion mutant, as progeny of selfs from this material segregate for id and An1. Conversely, an1-bz2-6923 appears to be a deletion mutant. The extent of the deletion is not defined although Id (two map units proximal to An1) and Ad (two map units distal from Bz2) are unaffected by the deletion.

Southern Analysis

Total DNA was extracted from leaf tissue by the urea extraction method (Dellaporta et al., 1983). Southern blots were performed as previously described (Johal, 1992) using Duralose-UV membranes (Stratagene). Mu2 probes were synthesized by random priming (Amersham) a gel-eluted internal 650-bp AvaI-BstEII Mu1 fragment isolated from pA/B5 (Chandler, 1986). This internal Mu1 fragment contains regions of homology to Mu2, thus allowing for hybridization to both Mu1 and Mu2 sequences.

Cloning Protocol

The genomic DNA restriction fragment containing the Mu2 element judged to cause the an1-891339 mutation was electro-eluted following preparative agarose gel electrophoresis of SstI digested total DNA, dialyzed, and concentrated by ethanol precipitation. Precipitated fragments were pre-annealed to SstI restricted arms of the bacteriophage vector lambda sep6/lac5 (Meyerowitz, from Marteinssen, CSH) and packaged using Gigapack Gold (Stratagene). This library was screened for Mu2 containing phage, with the SstI insert of a plaque purified Mu2 containing clone then transferred to the bacteriophage vector Lambda-ZAPII (Stratagene). This insert and other clones used for probing or sequencing were all sub-cloned into the plasmid Bluescript SK+ and maintained in SURE cells (Stratagene).

cDNA Library Screening

Two cDNA libraries, which served as sources for An1 cDNAs, were prepared from the shoots of 14 day old light grown B73 seedlings, a gift from A. Barkan, University of Oregon (Barkan, 1991) and from whole kernels (30 DAP) of W22, a gift from Karen Cone, University of Missouri. Sequence data from a 2.8 kb An1 cDNA was generated by Loftstrand Labs Limited.

RNA Preparation and Northern Analysis

Total RNA was prepared as previously described (Chomczynski et al., 1987). PolyA$^+$RNA was enriched using PolyA-Tract System III (Promega) following the manufacturer's protocol. Northerns were run, blotted and probed as previously described (Johal, 1992) using 1.5 kb and 1.1 kb subclones of An1 cDNA to generate random primed probes.

Analysis of ent-Kaurene and Kaurene Synthetase Activity

Analysis of the in vivo accumulation of ent-kaurene in light grown maize seedlings was performed. Cell free assays of kaurene synthetase A and B activities were performed using immature siliques from Arabidopsis seedlings. (Bensen, 1995).

Production of a Transgenic Plant

A transgenic plant containing a construct having a gene of the present invention can be regenerated from a culture transformed with that same construct, so long as plant species involved is susceptible to regeneration. "Culture" in this context comprehends an aggregate of cells, a callus, or derivatives thereof that are suitable for culture.

A plant is regenerated from a transformed cell or culture, or from an explant, by methods disclosed herein that are known to those of skill in the art. Methods vary according to the plant species. Seed is obtained from the regenerated plant or from a cross between the regenerated plant and a suitable plant of the same species using breeding methods known to those of skill in the art.

Example of Transformation Methods in Maize
(May be Modified for Specific Promoters and Structural Genes)

Maize Tapetum Specific Promoter: Stable Transformations
  Experimental Protocols
  Repetition 1,2, and 5;
Goal:
  Recover transgenic colonies, plants and progeny of maize resistant to Basta/Bialophos and expressing GUS driven by the tapetum specific SGB6g1 promoter
Genotype:
  54-68-5 B1-1 (Repetition 1) or
  54-68-5 161F3 (Repetition 2)
  54-68-5 161F4 (Repetition 5)
Medium:
  237 liquid suspension medium for maize
  115, callus maintenance medium for maize
  115E, callus 5 mg/L Basta selection medium
  115B, callus 3 mg/L Bialaphos selection medium
Tissue Treatment
  Sieve cells through 710 um mesh one day after subculture
  Resuspend in 237+3% PEG at 50 mg/ml plate density
  Incubate in 3% PEG overnight
  Plate cells, 0.5 ml/plate onto glass filters 934-AH atop a Whatman filter moistened with 1 ml 237+3% PEG medium
  Transfer cells on glass filter to 115 medium following bombardment
Particle gun bombardment
  DuPont helium gum (Repetitions 1 and 5)
  650 PSI rupture disks (Repetitions 1 and 5)
  DuPont PDS-1000 gun (Repetition 2)
  0.230" stopping plates, Acetyl macroprojectiles (Repetition 2)
  One bombardment per sample (Repetitions 1 and 5)
  Two bombardments per sample (Repetition 2)
  Pioneer tungsten modified DNA protocols, specific to each gun
DNA:
  DP687+DP610
  DP460+DP610
  DP1952+DP610
  DP2125+DP610
Treatment/Assay following bombardment
  Look for R gene expression 24–48 hours post bombardment
  Transfer samples to 115E (Repetition 1) 48 hours post bombardment. Transfer samples to 115B (Repetition 2 and 5) 7 days post bombardment
  Transfer cells off filters 2 weeks following transfer to selection
  PCR assay colonies for reporter gene prior to plant regeneration
  Maintain samples at 28C in the dark
Method of corn transformation to recover stable transgenic plants
Day-1
  Cells placed in liquid media and sieved (710 um), 100–200 mg of cells collected on 5.5 cm glass fiber filter over an area of 3.5 cm. Cells transferred to media and incubated media over night.
Day 0
  Filter and cells removed from media, dried and bombarded. Filter and cells placed back on media.
Day 5
  Cells on filter transferred to selection media (3 mg bialophos).
Day 12
  Cells on filter transferred to fresh selection media.
Day 19
  Cells scraped form filter and dispersed in 5 ml of selection media containing 0.6% low melting point sea plaque agarose. Cells and media spread over the surface of two 100 mm×15 mm plate containing 20 ml of gel-rite solidified media.
Day 40
  Putative transformants picked from plate.
Day 61
  Plates checked for new colonies.

REFERENCES

The references listed below are incorporated herein by reference to the extent that they supplement, explain, provide a background for or teach methodology, techniques or compositions employed herein.

Altschul et al. (1990). *J. Mol. Biol.* 215:403.

Barendse, G. W. M., Dijkstra, A. and Moore, T. C. (1983). The biosynthesis of the gibberellin precursor ent-kaurene in cell-free extracts and the endogenous gibberellins of Japanese morning glory in relation to seed development. *J.Plant Growth Regul.* 2, 165–175.

Barkan, A. and Marteinssen, R. A. (1991). *Proc. Natl. Acad. Sci. USA* 88, 3502.

Beavis, W. D., Grant, D., Albertsen, M. and Fincher, R. (1991). *Theor. Appl. Genet.* 83:141–145.

Bensen, R. J. et al. (1995) Cloning and characterization of the An1 gene, *The Plant Cell* 7:75–84.

Buckner, B., Kelson, T. L. and Robertson, D. S. (1990). *The Plant Cell* 2:867–876.

Chandler, V. L. and Walbot, V. (1986). DNA modification of a maize transposable element correlates with a loss of activity. *Proc. Natl. Acad. Sci. USA* 83:1767.

Cheng, P. C., Greyson, R. I. and Walden, D. B. (1983). Organ initiation and the development of unisexual flowers in then tassel and ear of zea mays. *Amer. J. Bot.* 70, 450–462.

Chomczynski, P. and Sacchi, N. (1987). *Anal. Bioechem.* 162, 156.

Coolbaugh, R. C. (1985). Sites of gibberellin biosynthesis in pea seedlings. *Plant Physiol.* 78, 655–657.

Dellaporta, S. L., Wood, J. B. and Hicks, J. B. (1983). *Plant Mol. Biol. Rep.* 1, 18.

Duncan, J. D. and West, C. A. (1981). Properties of kaurene synthetase from *Marah macroecarpus* endosperm: evidence for the participation of separate but interacting enzymes. *Plant Physiol.* 68, 1128–1134.

Emerson, R. A. and Emerson, S. E. (1922). Genetic interrelations of two andromonecious types of maize. *Genetics* 7, 203–227.

Facchini, P. and Chappell, J. (1992). Gene family for an elicitor-induced sesquiterpene cyclase in tobacco. *Proc. Natl. Acad. Sci. USA* 89, 11088–11092.

Fujioka, S., Yamane, H., Spray, C. R., Gaskin, P., MacMillain, J., Phinney, B. O. and Takahashi, N. (1988). Qualitative and quantitative analysis of gibberellins in vegetative shoots of normal, dwarf-1, dwarf-2, dwarf-3, and dwarf-5 seedlings of *Zea mays. L. Plant Physiol.* 88:1367–1372.

Han, C. d., Coe, Jr., E. H. and Marteinssen, R. A. (1992). *EMBO* 11:4037–4046.

Hedden, P., Phinney, B. O., Heupel, R., Fujii, D., Cohen, H., Gaskin, P., MacMillian, J. and Graebe, J. E. (1982). Hormones of young tassels of *Zea mays. Phytochemistry* 21:391–393.

Johal, G. S. and Briggs, S. P. (1992). Reductase activity encoded by the HM1 disease resistance gene in maize. *Science* 258:985–987.

McCarty, D. R., Carlson, C. B., Stinard, P. S. and Robertson, D. S. (1989). *The Plant Cell* 1:523–532.

McLaughlin, M. and Walbot, V. (1987). *Genetics* 117:771–776.

Marteinssen, R. A., Barkan, A., Freeling, M. and Taylor, W. C. (1989). *EMBOJ* 8:1633–1639.

Matthews, B. F., Wadsworth, G., Gebhardt, J. S. and Wilson, B. (1993). Cloning and expression of genes encoding aspartate aminotransferase in soybean. *Improved Crop and Plant Products Through Biotechnology*, Abs. X1–324, pp. 105.

Metzger, J. D. and Zeevart, J. A. D. (1980). Effect of photoperiod on the levels of endogenous gibberellins in spinach as measured by combined gas chromatography-selected ion current monitoring. *Plant Physiol.* 66, 844–846.

Metzger, J. D. and Zeevart, J. A. D. (1982). Photoperiodic control of gibberellin metabolism in spinach. *Plant Physiol.* 69, 287–291.

O'Reilly, C. O., Shepherd, N. S., Pereira, A., Schwartz-Summer, Z., Bertram, I., Robertson, D. S., Peterson, P. A. and Saedler, H. (1985). *EMBOJ* 4:877–882.

Pasternak et al. (1993). Sequence Similarity Searches, Multiple Sequence Alignments, and Molecular Tree Building in *Methods in Plant Molecular Biology and Biotechnology* Glick et al. (eds.), (CRC Press), pp. 251–267.

Rood, S. B., Buzzell, R. I., Mauder, L. N., Pearce, D. and Pharis, R. P. (1988). *Science* 241:1216–1218.

Simcox, P. D., Dennis, D. T. and West, C. A. (1975). Kaurene synthetase from plastids of developing plant tissues. *Biochem. Biophys. Res. Comm.* 66:166–172.

Sun, Goodman and Ausubel (1992). *The Plant Cell* 4:119–128.

Suzuki, Y., Yamane, H., Spray, C. R., Gaskin, P., MacMillian, J. and Phinney, B. O. (1992). Metabolism of ent-kaurene to gibberellin $A_{12}$-aldehyde in young shoots of normal maize. *Plant Physiol.* 98, 602–610.

Walbot, V. and Warren, C. (1988). Regulation of Mu element copy number in maize lines with an active or inactive transposable element system. *Mol. Gen. Genet.* 211:27–34.

Walbot, V. (1992). Strategies for mutagenesis and gene cloning using transposon tagging and T-DNA insertional mutagenesis. Ann. Rev. Plant Physiol. 43:49–82.

PCT patent application WO/9316096.

What is claimed is:

1. An isolated DNA molecule capable of hybridizing to a DNA molecule having the An2 nucleotide sequence shown in FIG. 6 (SEQ ID NO:8) under conditions of high stringency, wherein said DNA molecule encodes a product necessary for the conversion of GGPP to ent-kaurene in the biosynthesis of gibberellic acid.

2. An An2 gene cloned from maize.

3. An expression vector comprising:
    (a) an isolated DNA molecule capable of hybridizing with a DNA molecule having the An1 nucleotide sequence of FIG. 3 (SEQ ID NO: 6) under conditions of high stringency, wherein said DNA molecule encodes a product necessary for the conversion of GGPP to ent-kaurene in the biosynthesis of gibberellic acid, and
    (b) the promoter set forth in FIGS. 8A and 8B,
    wherein said promoter controls the expression of said DNA molecule.

4. The isolated DNA molecule of claim 1, having the nucleotide sequence of the An2 sequence shown in FIG. 6 (SEQ ID NO:8).

5. A polypeptide encoded by the DNA molecule of claim 4.

6. An expression vector comprising the DNA molecule of claim 1 and a promoter controlling expression of the molecule.

7. The expression vector of claim 6, wherein the promoter is the promoter set forth in FIGS. 8A and 8B.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

(x i) SEQUENCE DESCRIPTION: SEQ ID NO:1:

TTGCCAAGCT CTGCATCAGC TTGAGTGT 28

(2) INFORMATION FOR SEQ ID NO:2:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:2:

GGAAACATGT CTATCGATCA TATGTTGTGG GGA 33

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:3:

CTTCGAGATC GCCTTCCCTT CTCTCA 26

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:4:

TAGCCCAGCA AATCCCATCT TCAGTCCA 28

(2) INFORMATION FOR SEQ ID NO:5:

(i) SEQUENCE CHARACTERISTICS:
        (A) LENGTH: 823 amino acids
        (B) TYPE: amino acid
        (D) TOPOLOGY: linear (x i) SEQUENCE DESCRIPTION: SEQ ID NO:5:

```
Met Pro Tyr Pro His Pro Tyr Pro Trp Gln Ser Ser Arg Arg Arg
 1               5                  10                  15

Arg Arg Arg Gly Arg Asp Gly Ala Pro Arg Gln Pro Gln Ala Arg Arg
            20              25              30

Val Val Glu Arg Ala Ala Ala Gly Pro Gly His Ala Thr Thr Thr Gln
        35                  40                  45

Gln Pro Asp Asn Val Ser Ser Ala Lys Val Phe Gln Thr Ser Arg Val
    50                  55                  60

Glu Thr Glu Ser Lys Leu Arg Asn Gly Arg Lys Pro Gln Asp Leu Glu
65                  70                  75                  80

Asp Glu His Gln Ala Glu Glu Ala Glu Leu Gln Pro Leu Ile Asp Gln
                85                  90                  95

Val Arg Ala Met Leu Arg Ser Met Asn Asp Gly Asp Thr Ser Ala Ser
                100                 105                 110
```

```
Ala Tyr Asp Thr Ala Trp Val Ala Met Val Pro Lys Val Gly Gly Asp
        115                 120                 125

Gly Gly Ala Gln Pro Gln Phe Pro Ala Thr Val Arg Trp Ile Val Asp
    130                 135                 140

His Gln Leu Pro Asp Gly Ser Trp Gly Asp Ser Ala Leu Phe Ser Ala
145                 150                 155                 160

Tyr Asp Arg Met Ile Asn Thr Leu Ala Cys Val Val Ala Leu Thr Lys
                165                 170                 175

Trp Ser Leu Glu Pro Ala Arg Cys Glu Ala Gly Leu Ser Phe Leu His
                180                 185                 190

Glu Asn Met Trp Arg Leu Ala Glu Glu Ala Glu Ser Met Pro Ile
                195                 200                 205

Gly Phe Glu Ile Ala Phe Pro Ser Leu Ile Gln Thr Ala Arg Asp Leu
        210                 215                 220

Gly Val Val Asp Phe Pro Tyr Gly His Pro Ala Leu Gln Ser Ile Tyr
225                 230                 235                 240

Ala Asn Arg Glu Val Lys Leu Lys Arg Ile Pro Arg Asp Met Met His
                245                 250                 255

Arg Val Pro Thr Ser Ile Leu His Ser Leu Glu Gly Met Pro Asp Leu
                260                 265                 270

Asp Trp Pro Arg Leu Leu Asn Leu Gln Ser Cys Asp Gly Ser Phe Leu
            275                 280                 285

Phe Ser Pro Ser Ala Thr Ala Tyr Ala Leu Met Gln Thr Gly Asp Lys
    290                 295                 300

Lys Cys Phe Glu Tyr Ile Asp Arg Ile Val Lys Lys Phe Asn Gly Gly
305                 310                 315                 320

Val Pro Asn Val Tyr Pro Val Asp Leu Phe Glu His Ile Trp Val Val
                325                 330                 335

Asp Arg Leu Glu Arg Leu Gly Ile Ser Arg Tyr Phe Gln Arg Glu Ile
            340                 345                 350

Glu Gln Cys Met Asp Tyr Val Asn Arg His Trp Thr Glu Asp Gly Ile
        355                 360                 365

Cys Trp Ala Arg Lys Ser Asn Val Lys Asp Val Asp Thr Ala Met
    370                 375                 380

Ala Phe Arg Leu Leu Arg Leu His Gly Tyr Asn Val Ser Pro Ser Val
385                 390                 395                 400

Phe Lys Asn Phe Glu Lys Asp Gly Glu Phe Phe Cys Phe Val Gly Gln
                405                 410                 415

Ser Thr Gln Ala Val Thr Gly Met Tyr Asn Leu Asn Arg Ala Ser Gln
            420                 425                 430

Ile Ser Phe Gln Gly Glu Asp Val Leu His Arg Ala Arg Val Phe Ser
        435                 440                 445

Tyr Glu Phe Leu Arg Gln Arg Glu Glu Gln Gly Met Ile Arg Asp Lys
    450                 455                 460

Trp Ile Val Ala Lys Asp Leu Pro Gly Glu Val Gln Tyr Thr Leu Asp
465                 470                 475                 480

Phe Pro Trp Tyr Ala Ser Leu Pro Arg Val Glu Ala Arg Thr Tyr Leu
                485                 490                 495

Asp Gln Tyr Gly Gly Lys Asp Asp Val Trp Ile Gly Lys Thr Leu Tyr
            500                 505                 510

Arg Met Pro Leu Val Asn Asn Asp Thr Tyr Leu Glu Leu Ala Ile Arg
        515                 520                 525

Asp Phe Asn His Cys Gln Ala Leu His Gln Leu Glu Cys Asn Gly Leu
    530                 535                 540
```

| Gln | Thr | Trp | Tyr | Lys | Asp | Asn | Cys | Leu | Asp | Ala | Phe | Gly | Val | Glu | Pro |
| 545 | | | | 550 | | | | 555 | | | | | | | 560 |
| Gln | Asp | Val | Leu | Arg | Ser | Tyr | Phe | Leu | Ala | Ala | Cys | Ile | Phe | Glu |
| | | | | 565 | | | | 570 | | | | 575 | | |
| Pro | Ser | Arg | Ala | Ala | Glu | Arg | Leu | Ala | Trp | Ala | Arg | Thr | Ser | Met | Ile |
| | | | 580 | | | | | 585 | | | | | 590 | | |
| Ala | Asn | Ala | Ile | Ser | Thr | His | Leu | Arg | Asp | Ile | Ser | Glu | Asp | Lys | Lys |
| | | | 595 | | | | 600 | | | | | 605 | | | |
| Arg | Leu | Glu | Cys | Phe | Val | His | Cys | Leu | Tyr | Glu | Glu | Asn | Asp | Val | Ser |
| | | 610 | | | | 615 | | | | | 620 | | | | |
| Trp | Leu | Lys | Arg | Asn | Pro | Asn | Asp | Val | Ile | Leu | Glu | Arg | Ala | Leu | Arg |
| 625 | | | | | 630 | | | | | 635 | | | | | 640 |
| Arg | Leu | Ile | Asn | Leu | Leu | Ala | Gln | Glu | Ala | Leu | Pro | Ile | His | Glu | Gly |
| | | | | 645 | | | | | 650 | | | | | 655 | |
| Gln | Arg | Phe | Ile | His | Ser | Leu | Leu | Ser | Leu | Ala | Trp | Thr | Glu | Trp | Met |
| | | | 660 | | | | | 665 | | | | | 670 | | |
| Leu | Gln | Lys | Ala | Asn | Lys | Glu | Glu | Asn | Lys | Tyr | His | Lys | Cys | Ser | Gly |
| | | 675 | | | | | 680 | | | | | 685 | | | |
| Ile | Glu | Pro | Gln | Tyr | Met | Val | His | Asp | Arg | Gln | Thr | Tyr | Leu | Leu | Leu |
| | 690 | | | | | 695 | | | | | 700 | | | | |
| Val | Gln | Val | Ile | Glu | Ile | Cys | Ala | Gly | Arg | Ile | Gly | Glu | Ala | Val | Ser |
| 705 | | | | | 710 | | | | | 715 | | | | | 720 |
| Met | Ile | Asn | Asn | Lys | Asp | Asn | Asp | Trp | Phe | Ile | Gln | Leu | Thr | Cys | Ala |
| | | | | 725 | | | | | 730 | | | | | 735 | |
| Thr | Cys | Asp | Ser | Leu | Asn | His | Arg | Met | Leu | Leu | Ser | Gln | Asp | Thr | Met |
| | | | 740 | | | | | 745 | | | | | 750 | | |
| Lys | Asn | Glu | Ala | Arg | Ile | Asn | Trp | Ile | Glu | Lys | Glu | Ile | Glu | Leu | Asn |
| | | | 755 | | | | | 760 | | | | | 765 | | |
| Met | Gln | Glu | Leu | Ala | Gln | Ser | Leu | Leu | Leu | Arg | Cys | Asp | Glu | Lys | Thr |
| | | 770 | | | | 775 | | | | | 780 | | | | |
| Ser | Asn | Lys | Lys | Thr | Lys | Lys | Thr | Leu | Trp | Asp | Val | Leu | Arg | Ser | Leu |
| 785 | | | | | 790 | | | | | 795 | | | | | 800 |
| Tyr | Tyr | Ala | Thr | His | Ser | Pro | Gln | His | Met | Ile | Asp | Arg | His | Val | Ser |
| | | | | 805 | | | | | 810 | | | | | 815 | |
| Arg | Val | Ile | Phe | Glu | Pro | Val |
| | | | 820 | | | |

(2) INFORMATION FOR SEQ ID NO:6:

(i) SEQUENCE CHARACTERISTICS:
        (A) LENGTH: 802 amino acids
        (B) TYPE: amino acid
        (D) TOPOLOGY: linear (xi) SEQUENCE DESCRIPTION: SEQ ID NO:6:

| Met | Ser | Leu | Gln | Tyr | His | Val | Leu | Asn | Ser | Ile | Pro | Ser | Thr | Thr | Phe |
| 1 | | | | 5 | | | | | 10 | | | | | 15 | |
| Leu | Ser | Ser | Thr | Lys | Thr | Thr | Ile | Ser | Ser | Phe | Leu | Thr | Ile | Ser |
| | | | 20 | | | | | 25 | | | | | 30 | |
| Gly | Ser | Pro | Leu | Asn | Val | Ala | Arg | Asp | Lys | Ser | Arg | Ser | Gly | Ser | Ile |
| | | 35 | | | | | 40 | | | | | 45 | | | |
| His | Cys | Ser | Lys | Leu | Arg | Thr | Gln | Glu | Tyr | Ile | Asn | Ser | Gln | Glu | Val |
| | 50 | | | | | 55 | | | | | 60 | | | | |
| Gln | His | Asp | Leu | Pro | Leu | Ile | His | Glu | Trp | Gln | Gln | Leu | Gln | Gly | Glu |
| 65 | | | | 70 | | | | | 75 | | | | | | 80 |

```
Asp  Ala  Pro  Gln  Ile  Ser  Val  Gly  Ser  Asn  Ser  Asn  Ala  Phe  Lys  Glu
               85                      90                      95

Ala  Val  Lys  Ser  Val  Lys  Thr  Ile  Leu  Arg  Asn  Leu  Thr  Asp  Gly  Glu
               100                     105                     110

Ile  Thr  Ile  Ser  Ala  Tyr  Asp  Thr  Ala  Trp  Val  Ala  Leu  Ile  Asp  Ala
               115                     120                     125

Gly  Asp  Lys  Thr  Pro  Ala  Phe  Pro  Ser  Ala  Val  Lys  Trp  Ile  Ala  Glu
     130                     135                     140

Asn  Gln  Leu  Ser  Asp  Gly  Ser  Trp  Gly  Asp  Ala  Tyr  Leu  Phe  Ser  Tyr
145                     150                     155                          160

His  Asp  Arg  Leu  Ile  Asn  Thr  Leu  Ala  Cys  Val  Val  Ala  Leu  Arg  Ser
               165                     170                     175

Trp  Asn  Leu  Phe  Pro  His  Gln  Cys  Asn  Lys  Gly  Ile  Thr  Phe  Phe  Arg
               180                     185                     190

Glu  Asn  Ile  Gly  Lys  Leu  Glu  Asp  Glu  Asn  Asp  Glu  His  Met  Pro  Ile
               195                     200                     205

Gly  Phe  Glu  Val  Ala  Phe  Pro  Ser  Leu  Leu  Glu  Ile  Ala  Arg  Gly  Ile
     210                     215                     220

Asn  Ile  Asp  Val  Pro  Tyr  Asp  Ser  Pro  Val  Leu  Lys  Asp  Ile  Tyr  Ala
225                     230                     235                          240

Lys  Lys  Glu  Leu  Lys  Leu  Thr  Arg  Ile  Pro  Lys  Glu  Ile  Met  His  Lys
               245                     250                     255

Ile  Pro  Thr  Thr  Leu  Leu  His  Ser  Leu  Glu  Gly  Met  Arg  Asp  Leu  Asp
               260                     265                     270

Trp  Glu  Lys  Leu  Leu  Lys  Leu  Gln  Ser  Gln  Asp  Gly  Ser  Phe  Leu  Phe
               275                     280                     285

Ser  Pro  Ser  Ser  Thr  Ala  Phe  Ala  Phe  Met  Gln  Thr  Arg  Asp  Ser  Asn
     290                     295                     300

Cys  Leu  Glu  Tyr  Leu  Arg  Asn  Ala  Val  Lys  Arg  Phe  Asn  Gly  Gly  Val
305                     310                     315                          320

Pro  Asn  Val  Phe  Pro  Val  Asp  Leu  Phe  Glu  His  Ile  Trp  Ile  Val  Asp
               325                     330                     335

Arg  Leu  Gln  Arg  Leu  Gly  Ile  Ser  Arg  Tyr  Phe  Glu  Glu  Glu  Ile  Lys
               340                     345                     350

Glu  Cys  Leu  Asp  Tyr  Val  His  Arg  Tyr  Trp  Thr  Asp  Asn  Gly  Ile  Cys
               355                     360                     365

Trp  Ala  Arg  Cys  Ser  His  Val  Gln  Asp  Ile  Asp  Asp  Thr  Ala  Met  Ala
     370                     375                     380

Phe  Arg  Leu  Leu  Arg  Gln  His  Gly  Tyr  Gln  Val  Ser  Ala  Asp  Val  Phe
385                     390                     395                          400

Lys  Asn  Phe  Glu  Lys  Glu  Gly  Glu  Phe  Phe  Cys  Phe  Val  Gly  Gln  Ser
               405                     410                     415

Asn  Gln  Ala  Val  Thr  Gly  Met  Phe  Asn  Leu  Tyr  Arg  Ala  Ser  Gln  Leu
               420                     425                     430

Ala  Phe  Pro  Arg  Glu  Glu  Ile  Leu  Lys  Asn  Ala  Lys  Glu  Phe  Ser  Tyr
               435                     440                     445

Asn  Tyr  Leu  Leu  Glu  Lys  Arg  Glu  Arg  Glu  Glu  Leu  Ile  Asp  Lys  Trp
     450                     455                     460

Ile  Ile  Met  Lys  Asp  Leu  Pro  Gly  Glu  Ile  Gly  Phe  Ala  Leu  Glu  Ile
465                     470                     475                          480

Pro  Trp  Tyr  Ala  Ser  Leu  Pro  Arg  Val  Glu  Thr  Arg  Phe  Tyr  Ile  Asp
               485                     490                     495

Gln  Tyr  Gly  Gly  Glu  Asn  Asp  Val  Trp  Ile  Gly  Lys  Thr  Leu  Tyr  Arg
     500                     505                     510
```

```
            Met  Pro  Tyr  Val  Asn  Asn  Asn  Gly  Tyr  Leu  Glu  Leu  Ala  Lys  Gln  Asp
                      515                520                     525

Tyr  Asn  Asn  Cys  Gln  Ala  Gln  His  Gln  Leu  Glu  Trp  Asp  Ile  Phe  Gln
                 530                535                          540

Lys  Trp  Tyr  Glu  Glu  Asn  Arg  Leu  Ser  Glu  Trp  Gly  Val  Arg  Arg  Ser
            545                     550                     555                          560

Glu  Leu  Leu  Glu  Cys  Tyr  Tyr  Leu  Ala  Ala  Ala  Thr  Ile  Phe  Glu  Ser
                                565                     570                     575

Glu  Arg  Ser  His  Glu  Arg  Met  Val  Trp  Ala  Lys  Ser  Ser  Val  Leu  Val
                           580                585                          590

Lys  Ala  Ile  Ser  Ser  Ser  Phe  Gly  Glu  Ser  Ser  Asp  Ser  Arg  Arg  Ser
                      595                     600                     605

Phe  Ser  Asp  Gln  Phe  His  Glu  Tyr  Ile  Ala  Asn  Ala  Arg  Arg  Ser  Asp
                      610                615                     620

His  His  Phe  Asn  Asp  Arg  Asn  Met  Arg  Leu  Asp  Arg  Pro  Gly  Ser  Val
            625                     630                     635                          640

Gln  Ala  Ser  Arg  Leu  Ala  Gly  Val  Leu  Ile  Gly  Thr  Leu  Asn  Gln  Met
                                645                     650                     655

Ser  Phe  Asp  Leu  Phe  Met  Ser  His  Gly  Arg  Asp  Val  Asn  Asn  Leu  Leu
                           660                     665                     670

Tyr  Leu  Ser  Trp  Gly  Asp  Trp  Met  Glu  Lys  Trp  Lys  Leu  Tyr  Gly  Asp
                      675                     680                     685

Glu  Gly  Glu  Gly  Glu  Leu  Met  Val  Lys  Met  Ile  Ile  Leu  Met  Lys  Asn
                      690                     695                     700

Asn  Asp  Leu  Thr  Asn  Phe  Phe  Thr  His  Thr  His  Phe  Val  Arg  Leu  Ala
            705                     710                     715                          720

Glu  Ile  Ile  Asn  Arg  Ile  Cys  Leu  Pro  Arg  Gln  Tyr  Leu  Lys  Ala  Arg
                                725                     730                     735

Arg  Asn  Asp  Glu  Lys  Glu  Lys  Thr  Ile  Lys  Ser  Met  Glu  Lys  Glu  Met
                           740                     745                     750

Gly  Lys  Met  Val  Glu  Leu  Ala  Leu  Ser  Glu  Ser  Asp  Thr  Phe  Arg  Asp
                      755                     760                     765

Val  Ser  Ile  Thr  Phe  Leu  Asp  Val  Ala  Lys  Ala  Phe  Tyr  Tyr  Phe  Ala
                      770                     775                     780

Leu  Cys  Gly  Asp  His  Leu  Gln  Thr  His  Ile  Ser  Lys  Val  Leu  Phe  Gln
            785                     790                     795                          800

Lys  Val
```

( 2 ) INFORMATION FOR SEQ ID NO:7:

( i ) SEQUENCE CHARACTERISTICS:
        ( A ) LENGTH: 2784 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:7:

```
GAATTCCGCT  AGCTCTTGCT  TTGTTGTGTG  TCCTGATGGT  CGAGTTCCTC  ACCGTGCTTT       60

TGCTTTTCTG  CTTTCACTTG  CCTGCAGCTG  CAGCTCGTCA  ATCAGGTCCA  TGCCGTATCC      120

GCATCCGTAT  CCGTGGCAAA  GCAGCAGGAG  GAGGAGGAGG  AGGCGCGGGC  GCGACGGGGC      180

CCCGCGGCAG  CCTCAGGCTC  GCCGGGTGGT  GGAGCGCGCA  GCAGCAGGCC  CCGGCCACGC      240

GACGACAACG  CAGCAGCCCG  ACAACGTCTC  CAGTGCTAAA  GTGTTCCAGA  CCAGCCGTGT      300

GGAAACCGAG  TCGAAATTGC  GAAATGGCAG  GAAACCACAA  GACCTTGAGG  ATGAGCACCA      360
```

| | | | | | |
|---|---|---|---|---|---|
| GGCTGAGGAG | GCAGAGCTGC | AGCCACTTAT | CGACCAGGTG | AGGGCGATGC | TACGGTCGAT | 420 |
| GAACGACGGG | GATACCAGCG | CCTCGGCGTA | CGACACGGCG | TGGGTGGCGA | TGGTGCCGAA | 480 |
| GGTGGGCGGC | GACGGCGGCG | CCCAGCCCCA | GTTCCCGGCC | ACCGTGCGCT | GGATCGTGGA | 540 |
| CCACCAGCTG | CCCGACGGCT | CCTGGGGCGA | CTCGGCCCTG | TTCTCCGCCT | ACGACCGCAT | 600 |
| GATCAACACC | CTCGCCTGCG | TCGTCGCGCT | GACCAAGTGG | TCGCTGGAGC | CCGCGAGGTG | 660 |
| CGAGGCGGGG | CTCTCGTTCC | TGCACGAGAA | CATGTGGAGG | CTAGCGGAGG | AGGAGGCGGA | 720 |
| GTCGATGCCC | ATCGGCTTCG | AGATCGCCTT | CCCTTCTCTC | ATCCAGACGG | CTAGGGACCT | 780 |
| GGGCGTCGTC | GACTTCCCGT | ACGGACACCC | GGCGCTGCAG | AGCATATACG | CCAACAGGGA | 840 |
| AGTCAAGCTG | AAGCGGATCC | CAAGGGACAT | GATGCACAGG | GTCCCGACGT | CCATCCTGCA | 900 |
| CAGCCTTGAA | GGGATGCCTG | ACCTGGACTG | GCCGAGGCTT | CTGAACCTCC | AGTCCTGCGA | 960 |
| CGGCTCCTTC | TTGTTCTCTC | CTTCGGCTAC | CGCTTACGCG | CTGATGCAAA | CCGGTGACAA | 1020 |
| GAAGTGCTTC | GAATACATCG | ACAGGATTGT | CAAAAAATTC | AACGGGGAG | TCCCCAATGT | 1080 |
| TTATCCGGTC | GATCTTTTCG | AGCACATCTG | GTTGTGGAT | CGGTTGGAGC | GACTCGGGAT | 1140 |
| CTCCCGCTAC | TTCCAACGAG | AGATTGAGCA | GTGCATGGAC | TATGTGAACA | GGCACTGGAC | 1200 |
| TGAAGATGGG | ATTTGCTGGG | CTAGGAAATC | CAATGTGAAG | GATGTGGATG | ACACAGCTAT | 1260 |
| GGCTTTCCGA | CTACTAAGGC | TACATGGATA | CAATGTCTCT | CCAAGTGTGT | TTAAGAACTT | 1320 |
| TGAGAAAGAT | GGAGAGTTCT | TTTGTTTTGT | GGGCCAATCG | ACTCAAGCCG | TCACTGGGAT | 1380 |
| GTATAACCTC | AACAGAGCCT | CTCAGATAAG | TTTTCAAGGA | GAGGATGTAT | TGCATCGTGC | 1440 |
| TAGGGTTTTC | TCGTATGAGT | TTCTGAGACA | GAGAGAAGAA | CAAGGCATGA | TCCGTGATAA | 1500 |
| ATGGATCGTT | GCCAAGGATC | TACCTGGCGA | GGTGCAATAT | ACACTAGACT | TCCCTTGGTA | 1560 |
| TGCAAGCTTG | CCTCGTGTAG | AGGCAAGAAC | CTATCTAGAT | CAATATGGTG | GTAAAGATGA | 1620 |
| CGTTTGGATT | GGAAAGACAC | TCTACAGGAT | GCCTCTTGTG | AATAACGACA | CATATCTAGA | 1680 |
| GTTGGCAATA | AGGGATTTCA | ACCATTGCCA | AGCTCTGCAT | CAGCTTGAGT | GTAATGGGCT | 1740 |
| GCAAACGTGG | TACAAGGATA | ATTGCCTTGA | CGCTTTTGGA | GTAGAACCAC | AAGATGTTTT | 1800 |
| AAGATCTTAC | TTTTTAGCTG | CTGCTTGCAT | TTTTGAACCT | AGCCGTGCTG | CTGAGCGGCT | 1860 |
| TGCATGGGCT | AGAACGTCAA | TGATTGCCAA | TGCCATTTCT | ACACATCTTC | GTGACATTTC | 1920 |
| GGAAGACAAG | AAGAGATTGG | AATGTTTCGT | GCACTGTCTC | TATGAAGAAA | ACGATGTATC | 1980 |
| ATGGCTTAAA | CGAAATCCTA | ATGATGTTAT | TCTTGAGAGG | GCACTTCGAA | GATTAATTAA | 2040 |
| CTTATTAGCA | CAAGAAGCAT | TGCCAATTCA | TGAAGGACAA | AGATTCATAC | ACAGTCTATT | 2100 |
| GAGTCTTGCA | TGGACCGAAT | GGATGTTGCA | AAAGGCAAAT | AAAGAAGAAA | ACAAATATCA | 2160 |
| CAAATGCAGT | GGTATAGAAC | CACAATACAT | GGTTCATGAT | AGGCAAACAT | ACTTACTTTT | 2220 |
| AGTTCAGGTT | ATTGAGATTT | GTGCTGGACG | AATTGGTGAG | GCTGTGTCAA | TGATAAACAA | 2280 |
| CAAGGATAAT | GATTGGTTTA | TTCAACTCAC | ATGTGCTACT | TGTGACAGTC | TTAACCATAG | 2340 |
| GATGTTACTG | TCCCAGGATA | CTATGAAGAA | TGAAGCAAGA | ATAAATTGGA | TTGAGAAGGA | 2400 |
| AATCGAGTTG | AATATGCAAG | AGCTTGCTCA | ATCTCTCCTT | TTGAGATGTG | ATGAGAAAAC | 2460 |
| TAGCAATAAG | AAGACCAAGA | AAACCTTATG | GGATGTCCTA | AGAAGTTTAT | ACTATGCTAC | 2520 |
| TCATTCCCCA | CAACATATGA | TCGATAGACA | TGTTTCCAGA | GTTATCTTTG | AGCCTGTTTA | 2580 |
| AAAATGTTTA | AGTGGTAGAC | CATTATGTTA | GGTGTAAATG | TGTACATAAA | AGTTATCATA | 2640 |
| AGGAGTAATG | GTAGCAGAAG | CATGCAGTTG | TAAGTTTATT | TGTTGCTTAG | AATAGAAATT | 2700 |
| AGTGTAGCTA | TAATATCAAG | AATGTTCCTA | TATAAGTAAT | CATATTATGG | ATAGAGGTGT | 2760 |

| | | | | | | |
|---|---|---|---|---|---|---|
| TCATATGAAT | AATAAAAAGG | AATC | | | | 2784 |

( 2 ) INFORMATION FOR SEQ ID NO:8:

( i ) SEQUENCE CHARACTERISTICS:
        ( A ) LENGTH: 488 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

| | | | | | | |
|---|---|---|---|---|---|---|
| CTTCGAGATC | GCCTTCCCTT | CTCTCATCGA | ACTAGCCAAG | AGTCTGGGCG | TGGACGACTT | 60 |
| CCCGTACGAC | CACCAGGCTT | TGCAGGGAAT | ATACTCGAGC | AGGGAGATCA | AGATGAAGAG | 120 |
| GATTCCTAAG | GAAGTGATGC | ACACGGTTCC | CACATCCATT | CTCCACAGCC | TGGAAGGGAT | 180 |
| GCCCGGGCTA | GACTGGGCGA | AGCTGCTGAA | ACTGCAGTCG | AGCGACGGGT | CCTTCCTCTT | 240 |
| CTCACCCGCG | GCCACCGCGT | ACGCTCTCAT | GAACACCGGC | GACGACAGGT | GCTTCAGCTA | 300 |
| CATCGACAGG | ACAGTCAAGA | AATTCAACGG | AGGAGTGCCC | AACGTCTACC | CCGTGGACCT | 360 |
| TTTCGAGCAC | ATATGGGCTG | TCGATCGCCT | GGAGCGTCTC | GGGATCTCCC | GCTACTTCCA | 420 |
| GAAAGAGATT | GAGCAGTGCA | TGGACTACGT | GAACAGGCAC | TGGACTGAAG | ATGGGATTTG | 480 |
| CTGGGCTA | | | | | | 488 |

( 2 ) INFORMATION FOR SEQ ID NO:9:

( i ) SEQUENCE CHARACTERISTICS:
        ( A ) LENGTH: 2520 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

| | | | | | | |
|---|---|---|---|---|---|---|
| GAATTCTTTT | AAAAAAATAA | CGTCTGTGCC | TCACAGTAGC | TGTAGGAGTA | GGGTGTTGCA | 60 |
| TCTCGCGCTT | CAATTCGGTC | GACAGCGGCT | CCTGTGGTCT | CCAGCCTTTA | CCGCTTTGGC | 120 |
| AACTGGTTCT | GTTTCAATCA | GGTCCATGCC | GTATCTTGCT | AAAGCTAAAA | ATAAATGCGT | 180 |
| TCACGGGAAC | GGCGTGTGTC | CGTGTTTCTG | CTCTGCTGCA | TGCAGCTCTC | GCCTTTATTT | 240 |
| TTTCTTTCCA | TCAAAAGCAA | CCGATGACCA | ACGGCCTTAC | ACAGTCTGTC | GAGAACTCGA | 300 |
| GATTCTCCAT | CCCCCCAAAT | GAAAACGAGG | TCGTAAATCT | CGCTTCACGT | CGGTAAGTCT | 360 |
| AAAAAATCTT | AAATTTAACT | GAACTTGTTA | AAGATATTGT | CAACATTTAG | ATGTTTAGTT | 420 |
| AAATTTACTA | TAAAAAAAGT | ATCTTAAGAT | ACGTCCATTC | AGTAAAAAAA | AAACAAAAAG | 480 |
| AAAAACTTTA | ACTATTCGAC | AAACGAGATT | TTTTTTTCCC | GGGTTGCCGT | CCCACTGCAC | 540 |
| GGACTAGTTG | CCAGGCATCT | TCCCTGAAAC | AAAAAGGAAA | ACACCAGTTC | TAGGCACGTA | 600 |
| CGTACTACGC | TTACGTGTAT | ATAAATATTT | ATCGGCTGTG | GACAGATTAT | AGAGGGCATC | 660 |
| TTGTTGCGAC | GGGGCGACGA | ATGTCCGTCT | CCAGCCACCC | GTCCGTTCGC | AAATCACGTA | 720 |
| CAAAGCTACT | TTGTGTTAGC | AGAAACAGCA | TAAAAAACAA | AATAGATCAA | CTAACAAATC | 780 |
| TGGAAGCACG | ACACATAAAT | TTACTTAAAA | ACCTTTCAAT | GAGAAAGGAA | AAATTATGAG | 840 |
| CACCAGCCAG | TTGATGTGAA | GTGTTTATGT | AACGTCGTTC | GTAGACGGCG | GCTTACAAGA | 900 |
| GAAGTAAAAA | GACGACGTGC | GATAAATTCT | AATTAGGTTC | ATTAATATAT | ACCTAAGTTT | 960 |
| TTGGACGATG | GGTATCCACT | CTGCTCGCTA | ATATTGTCTC | TATATTCAGA | ATTTGGATCA | 1020 |

-continued

| | | | | | | |
|---|---|---|---|---|---|---|
| CAAACTTAAT | AGTTTGGTTG | GTTATGTATA | CAGTATACTC | ACGCACCAAC | GCACGCACGC | 1080 |
| CGCGAGAAGG | ATTAGCGAAA | CGCTGGTGGT | TTTTTGTCCA | CTAGCCGGTG | CGTCCCCGCG | 1140 |
| CGGGAATCAT | TCGGGCCTGC | CTCTCTACTC | TGCTCCCAGC | TACTAGTCCC | TCACTCACTT | 1200 |
| CTCTCAGACT | TGTGTGTCTC | GTCCTATATA | TATATACACA | CGCTACGCTA | TAGCTGCTCA | 1260 |
| CACACATAGT | ATCGTCGTCT | CTCTCTCCTT | CCCACCAACA | ACGCACGCGT | CGAAGAAGGA | 1320 |
| AATGATTAGT | AGCAGCCATA | CTTGCTCCGC | CTATTAATAG | CCAGCGCGCG | CGTCTTGTTT | 1380 |
| TGCTCTCTTC | TGTTCTGTTT | TGCCCTAGAT | TAGCGGCGGC | GTTTTGGCCT | CGCGCGAACG | 1440 |
| TCTCGTCCTT | GCCGTCTCGC | GCGCGTGCGT | ACGTGCCTGC | ATTGCGATTT | GCAATTATTA | 1500 |
| GCATCGCGCG | GCGGCGGCGG | GCCGCCCATG | AAGCTCCTCT | CGCCGGCGGC | CGCACCGTCG | 1560 |
| TCCTCGCCGT | TGTTCCCTCC | TCGCATCGTC | GAAGGTACGT | GTACACCGTC | GTCAGCAGCT | 1620 |
| GCTACCTCCG | CGGCGCCGGC | CAGCCGAGGT | TCCATGATGC | CTATCTATCT | ATGTATAGTA | 1680 |
| CGTATATGGC | GCCGCGCCAG | GCCCTTGCCC | TTGTCGTCTG | CCTGCATGCC | TACTACTACA | 1740 |
| AGCTACTTCC | AAATTTCGCA | TTGTCCTCGG | CGCTACACGG | CCGGTGGGCA | ATCAGACAAA | 1800 |
| GAAACAAACG | TGTAAGCAAG | ATGAAAAATT | GTATTTTGG | GTTCGGACAA | GCAAGTCGTC | 1860 |
| GTCGTCGTCT | TAGGGTAGCC | ACACACACAG | GCAGATGGGC | AATCAGACAA | AGAAACAAAC | 1920 |
| ATAAGCAAGA | TGGAGAGAGG | CAGGCAGGCA | GTCAGGCGCT | GCTGCTGCTA | GTGCTAGCTC | 1980 |
| TTGCTTTGTT | GTGTGTCCTG | ATGGTCGAGT | TCCTCACCGC | TGCTTTTGCT | TTTCTGCTTT | 2040 |
| CACTTGCCTG | CAGCTGCAGC | TCGTCAATCA | GGTCCATGCC | GTATCCGCAT | CCGTATCCGT | 2100 |
| GGCAAAGCAG | CAGCAGCAGG | AGGAGGAGGA | GGCGCGGGCG | CGACGGGGCC | CCGCGGCAGC | 2160 |
| CTCAGGCTCG | CCGGGTGGTG | GAGAGCGCAG | CAGCAGGCCC | CGGCCACGGC | GACGACAACG | 2220 |
| CAGCAGCCTG | ACAACGTCTC | CAGTGCTAAA | GGTGCTAGCT | TGCTCGTTAT | ATTTGATTTG | 2280 |
| ACTAGTCTCA | TCATCCACCC | CCCAGTCACG | TACACAGATG | CTCTCTCTCT | CTCTCTCTCT | 2340 |
| TGAATTGATG | AGCGAACGAA | ACACTCAGAC | AGATGCTGCC | GTGCTGCAGT | NCGCCCGTAG | 2400 |
| CAGCACAGAC | ACTCTGCCGC | ACACACCTGC | GCTTGTCGCT | TCCCCTCTTG | CTATATCTCC | 2460 |
| TGCTGCTTTT | GCTAAAGCCG | GAAACCAAAA | AGAAAGTTGA | GCTTTTCGTC | ACAATTTTGC | 2520 |